US 8,588,892 B2

(12) United States Patent
Hladio et al.

(10) Patent No.: US 8,588,892 B2
(45) Date of Patent: Nov. 19, 2013

(54) METHOD AND SYSTEM FOR ALIGNING A PROSTHESIS DURING SURGERY USING ACTIVE SENSORS

(75) Inventors: Andre Novomir Hladio, Waterloo (CA); Armen Garo Bakirtzian, Montreal (CA); Uriah Lodewyk Antoine Van Amerom, Waterdown (CA)

(73) Assignee: Avenir Medical Inc., Waterloo (CA)

( * ) Notice: Subject to any disclaimer, the term of this patent is extended or adjusted under 35 U.S.C. 154(b) by 202 days.

(21) Appl. No.: 13/132,115

(22) PCT Filed: Dec. 2, 2009

(86) PCT No.: PCT/CA2009/001765
§ 371 (c)(1),
(2), (4) Date: Aug. 2, 2011

(87) PCT Pub. No.: WO2010/063117
PCT Pub. Date: Jun. 10, 2010

(65) Prior Publication Data
US 2012/0022406 A1      Jan. 26, 2012

Related U.S. Application Data

(60) Provisional application No. 61/200,669, filed on Dec. 2, 2008.

(51) Int. Cl.
| | | |
|---|---|---|
| *A61B 6/00* | (2006.01) | |
| *A61B 17/58* | (2006.01) | |
| *A61B 17/60* | (2006.01) | |
| *A61B 17/00* | (2006.01) | |
| *A61B 5/05* | (2006.01) | |
| *A61F 2/00* | (2006.01) | |
| *A61D 1/04* | (2006.01) | |

(52) U.S. Cl.
USPC ............ 600/431; 600/409; 606/102; 606/116

(58) Field of Classification Search
USPC .......... 600/409, 587, 594, 595, 431; 606/102, 606/116
See application file for complete search history.

(56) References Cited

U.S. PATENT DOCUMENTS

| | | | |
|---|---|---|---|
| 4,994,064 A | 2/1991 | Aboczky | |
| 5,122,145 A * | 6/1992 | Fishbane | 606/102 |
| 5,141,512 A * | 8/1992 | Farmer et al. | 606/87 |
| 5,227,985 A | 7/1993 | DeMenthon | |
| 5,249,581 A | 10/1993 | Horbal et al. | |
| 5,480,439 A * | 1/1996 | Bisek et al. | 128/898 |
| 5,611,353 A | 3/1997 | Dance et al. | |
| 5,700,268 A * | 12/1997 | Bertin | 606/102 |
| 5,772,610 A * | 6/1998 | McGorry et al. | 600/594 |
| 5,807,252 A | 9/1998 | Hassfeld et al. | |
| 5,854,843 A | 12/1998 | Jacknin et al. | |
| 5,880,976 A | 3/1999 | DiGioia III et al. | |
| 5,956,660 A | 9/1999 | Neumann | |
| 5,966,827 A * | 10/1999 | Horvath et al. | 33/512 |
| 6,061,644 A | 5/2000 | Leis | |
| 6,161,032 A * | 12/2000 | Acker | 600/424 |
| 6,395,005 B1 | 5/2002 | Lovell | |
| 6,450,978 B1 | 9/2002 | Brosseau et al. | |
| 6,607,487 B2 | 8/2003 | Chang et al. | |
| 6,711,431 B2 | 3/2004 | Sarin et al. | |
| 6,917,827 B2 | 7/2005 | Kienzle, III | |
| 6,925,339 B2 | 8/2005 | Grimm et al. | |
| 6,978,167 B2 | 12/2005 | Dekel et al. | |
| 6,988,009 B2 | 1/2006 | Grimm et al. | |
| 7,130,676 B2 | 10/2006 | Barrick | |
| 7,302,355 B2 | 11/2007 | Jansen et al. | |
| 7,314,048 B2 | 1/2008 | Couture et al. | |
| 7,392,076 B2 * | 6/2008 | Moctezuma de La Barrera | 600/427 |
| 7,400,246 B2 | 7/2008 | Breeding | |
| 7,407,054 B2 | 8/2008 | Seiler et al. | |
| 7,412,777 B2 | 8/2008 | Pelletier et al. | |
| 7,419,492 B2 * | 9/2008 | Yoon et al. | 606/91 |
| 7,427,272 B2 | 9/2008 | Richard et al. | |
| 7,431,736 B2 | 10/2008 | Maroney et al. | |
| 7,559,931 B2 | 7/2009 | Stone | |
| 7,588,571 B2 * | 9/2009 | Olsen | 606/57 |
| 7,594,933 B2 * | 9/2009 | Kammerzell et al. | 623/22.15 |
| 7,657,298 B2 | 2/2010 | Moctezuma de la Barrera et al. | |
| 7,668,584 B2 | 2/2010 | Jansen | |
| 7,753,921 B2 | 7/2010 | Leitner | |
| 7,769,429 B2 | 8/2010 | Hu | |
| 7,780,681 B2 | 8/2010 | Sarin et al. | |

| | | | |
|---|---|---|---|
| 7,840,256 B2 * | 11/2010 | Lakin et al. ............... 600/426 | |
| 7,876,942 B2 | 1/2011 | Gilboa | |
| 7,877,131 B2 | 1/2011 | Jansen et al. | |
| 7,885,705 B2 | 2/2011 | Murphy | |
| 7,927,338 B2 | 4/2011 | Laffargue et al. | |
| 7,970,190 B2 | 6/2011 | Steinle et al. | |
| 7,995,280 B2 | 8/2011 | Kuss et al. | |
| 8,000,926 B2 | 8/2011 | Roche et al. | |
| 8,007,448 B2 | 8/2011 | Moctezuma de La Barrera | |
| 8,034,057 B2 | 10/2011 | Penenberg | |
| 8,057,482 B2 * | 11/2011 | Stone et al. ............... 606/102 | |
| 8,152,726 B2 | 4/2012 | Amiot et al. | |
| 8,165,659 B2 | 4/2012 | Sheffer et al. | |
| 8,167,823 B2 | 5/2012 | Nyez et al. | |
| 8,177,850 B2 | 5/2012 | Rudan et al. | |
| 8,202,324 B2 | 6/2012 | Meulink et al. | |
| 8,206,405 B2 | 6/2012 | Beverland et al. | |
| 8,308,663 B2 | 11/2012 | Tuma et al. | |
| 8,337,426 B2 | 12/2012 | Nyez | |
| 8,425,557 B2 * | 4/2013 | Kuiper et al. ............... 606/247 | |
| 2002/0077540 A1 * | 6/2002 | Kienzle, III ............... 600/424 | |
| 2002/0087101 A1 | 7/2002 | Barrick et al. | |
| 2003/0069591 A1 | 4/2003 | Carson et al. | |
| 2003/0208296 A1 | 11/2003 | Brisson et al. | |
| 2004/0102792 A1 | 5/2004 | Sarin et al. | |
| 2004/0254586 A1 * | 12/2004 | Sarin et al. ............... 606/130 | |
| 2005/0021044 A1 | 1/2005 | Stone et al. | |
| 2005/0065617 A1 | 3/2005 | Moctezuma de la Barrera et al. | |
| 2005/0149050 A1 * | 7/2005 | Stifter et al. ............... 606/102 | |
| 2005/0245820 A1 | 11/2005 | Sarin | |
| 2005/0251026 A1 | 11/2005 | Stone | |
| 2005/0288609 A1 | 12/2005 | Warner et al. | |
| 2006/0004284 A1 | 1/2006 | Grunschlager et al. | |
| 2006/0084889 A1 * | 4/2006 | Drumm et al. ............... 600/587 | |
| 2006/0155382 A1 | 7/2006 | Katzman | |
| 2006/0189864 A1 | 8/2006 | Paradis et al. | |
| 2006/0190011 A1 | 8/2006 | Ries | |
| 2006/0293614 A1 | 12/2006 | Radinsky et al. | |
| 2007/0118139 A1 | 5/2007 | Cuellar et al. | |
| 2007/0225731 A1 | 9/2007 | Couture et al. | |
| 2007/0239281 A1 | 10/2007 | Gotte et al. | |
| 2007/0270686 A1 | 11/2007 | Ritter et al. | |
| 2008/0027312 A1 | 1/2008 | Dick | |
| 2008/0033442 A1 * | 2/2008 | Amiot et al. ............... 606/80 | |
| 2008/0051910 A1 * | 2/2008 | Kammerzell et al. ...... 623/22.21 | |
| 2008/0077004 A1 * | 3/2008 | Henning ............... 600/409 | |
| 2008/0125785 A1 | 5/2008 | Chana | |
| 2008/0132783 A1 * | 6/2008 | Revie et al. ............... 600/426 | |
| 2008/0146969 A1 | 6/2008 | Kurtz | |
| 2008/0172055 A1 | 7/2008 | Mollard et al. | |
| 2008/0183104 A1 * | 7/2008 | Tuma et al. ............... 600/587 | |
| 2008/0214960 A1 | 9/2008 | Hodgson et al. | |
| 2008/0228188 A1 * | 9/2008 | Birkbeck et al. ............... 606/87 | |
| 2008/0255584 A1 | 10/2008 | Beverland et al. | |
| 2008/0269596 A1 | 10/2008 | Revie et al. | |
| 2008/0294265 A1 | 11/2008 | Warkentine et al. | |
| 2008/0312529 A1 | 12/2008 | Amiot et al. | |
| 2008/0319313 A1 * | 12/2008 | Boivin et al. ............... 600/424 | |
| 2009/0099570 A1 | 4/2009 | Paradis et al. | |
| 2009/0125117 A1 | 5/2009 | Paradis et al. | |
| 2009/0143670 A1 | 6/2009 | Daigneault et al. | |
| 2009/0163930 A1 * | 6/2009 | Aoude et al. ............... 606/130 | |
| 2009/0171370 A1 * | 7/2009 | Yoon et al. ............... 606/130 | |
| 2009/0209343 A1 | 8/2009 | Foxlin et al. | |
| 2009/0248044 A1 | 10/2009 | Amiot et al. | |
| 2009/0281545 A1 | 11/2009 | Stubbs | |
| 2009/0289806 A1 * | 11/2009 | Thornberry ............... 340/686.1 | |
| 2009/0314925 A1 | 12/2009 | Van Vorhis et al. | |
| 2009/0316967 A1 | 12/2009 | Dardenne et al. | |
| 2010/0016705 A1 | 1/2010 | Stone | |
| 2010/0069911 A1 * | 3/2010 | Borja et al. ............... 606/88 | |
| 2010/0076505 A1 * | 3/2010 | Borja ............... 606/86 R | |
| 2010/0100011 A1 | 4/2010 | Roche | |
| 2010/0137871 A1 * | 6/2010 | Borja ............... 606/91 | |
| 2010/0153081 A1 | 6/2010 | Bellettre et al. | |
| 2010/0192961 A1 * | 8/2010 | Amiot et al. ............... 128/882 | |
| 2010/0261998 A1 | 10/2010 | Stiehl | |
| 2010/0299101 A1 | 11/2010 | Shimada et al. | |
| 2010/0312247 A1 | 12/2010 | Tuma | |
| 2011/0092858 A1 | 4/2011 | Burger et al. | |
| 2011/0213379 A1 * | 9/2011 | Blau et al. ............... 606/102 | |
| 2012/0022406 A1 | 1/2012 | Hadio et al. | |
| 2012/0029389 A1 | 2/2012 | Amiot et al. | |
| 2012/0065926 A1 | 3/2012 | Lee et al. | |
| 2012/0143084 A1 | 6/2012 | Shoham | |
| 2012/0157887 A1 | 6/2012 | Fanson et al. | |
| 2012/0209117 A1 | 8/2012 | Mozes et al. | |
| 2012/0232802 A1 | 9/2012 | Haimerl et al. | |
| 2012/0283599 A1 * | 11/2012 | Borja ............... 600/587 | |

FOREIGN PATENT DOCUMENTS

| | | |
|---|---|---|
| EP | 1563810 B1 | 3/2010 |
| FR | 2684287 A1 | 6/1993 |
| WO | 2006/109983 A1 | 10/2006 |
| WO | 2006128301 A1 | 12/2006 |
| WO | 2007084893 A2 | 7/2007 |
| WO | 2007095248 A2 | 10/2007 |
| WO | 2008151446 A1 | 12/2008 |
| WO | 2009062314 A1 | 5/2009 |
| WO | 2009117833 A1 | 10/2009 |
| WO | 2010030809 A1 | 3/2010 |
| WO | 2010063117 A1 | 6/2010 |
| WO | 2012080840 A1 | 6/2012 |

OTHER PUBLICATIONS

International Search Report and Written Opinion dated May 22, 2012, relating to PCT International Patent Application No. PCT/IB2011/003246 issued from the Canadian Intellectual Property Office.

Int'l Search Report issued on Feb. 18, 2010 in Int'l Application No. PCT/CA2009/001765.

Int'l Preliminary Report on Patentability issued Jun. 7, 2011 in Int'l Application No. PCT/CA2009/007165; Written Opinion.

Kanoh et al, "Accurate Acetabular Component Orientation After Total Hip Arthroplasty Using an Acetabular Alignment Guide," The Journal of Arthroplasty, vol. 00, No. 0, pp. 1-6 (2009).

Digioia III et al, "Comparison of a Mechanical Acetabular Alignment Guide With Computer Placement of the Socket," The Journal of Arthroplasty, vol. 17, No. 3, pp. 359-363 (2002).

Nogler et al, "Reduced variability in cup positioning: the direct anterior surgical approach using navigation," Acta Orthopaedica, vol. 79, No. 6, pp. 789-793 (2008).

Birrell et al, "Projecting the need for hip replacement over the next three decades: influence of changing demography and threshold for surgery," Annals of the Rheumatic Diseases, vol. 58, pp. 569-572 (1999).

Seidel et al, "Hip joint center location from palpable bony landmarks—a cadaver study," Journal of Biomechanics, vol. 28, No. 8, pp. 995-998 (1995).

Solomon et al, "Surgical Anatomy for Pelvic External Fixation," Clinical Anatomy, vol. 21, pp. 674-682 (2008).

Digioia III et al, "Surgical Navigation for Total Hip Replacement With the Use of HIPNAV," Operative Techniques in Orthopaedics, vol. 10, No. 1, pp. 3-8 (2000).

* cited by examiner

*Primary Examiner* — Brian Szmal
*Assistant Examiner* — May Abouelela
(74) *Attorney, Agent, or Firm* — Gowling Lafleur Henderson LLP

(57) ABSTRACT

A method and system for determining the orientation of a surgical tool with respect to a bone of a patient, and a device for positioning a sensor are disclosed. The bone has at least three predetermined reference locations. The method includes: (a) defining a reference plane based on distances between the at least three predetermined reference locations;

(b) determining a first sensing location on the bone based on the at least three predetermined reference locations; (c) attaching a first active sensor to the bone at the first sensing location; (d) positioning the surgical tool proximate the bone, the surgical tool including a second active sensor; (e) sensing movement of the bone using the first active sensor; (T) transmitting first information relating to movement of the bone using the first active sensor; (g) sensing movement of the surgical tool using the second active sensor; (h) transmitting second information relating to movement of the surgical tool using the second active sensor; (i) receiving the first and second information from the first and second active sensors; and (j) determining a three-dimensional orientation of the surgical tool with respect to the reference plane based on the first and second information. In some cases, the method may further include displaying the three dimensional orientation information to the user on a display device.

23 Claims, 17 Drawing Sheets

METHOD AND SYSTEM FOR ALIGNING A PROSTHESIS DURING SURGERY USING ACTIVE SENSORS

CROSS-REFERENCE TO RELATED APPLICATION

This application is a Section 371 of International Application No. PCT/CA2009/001765, filed Dec. 2, 2009, which was published in the English language on Jun. 10, 2010, under International Publication No. WO 2010/063117 A1, and the disclosure of which is incorporated herein by reference.

TECHNICAL FIELD

The present invention relates to aligning a prosthesis during surgery. In particular, the invention relates to methods and systems for aligning a prosthesis during surgery using active sensors, as well as a device for positioning a sensor.

BACKGROUND

Total hip arthroplasty (THA), also known as total hip replacement (THR), is the surgical replacement of the hip joint with an artificial prosthesis. The procedure involves the surgical excision of the head and proximal neck of the femur and removal of the acetabular cartilage and subchondral bone. An artificial canal is created in the proximal medullary region of the femur, and a metal femoral prosthesis is inserted into the femoral medullary canal. An acetabular component or implant is inserted proximally in the enlarged acetabular space.

THA is one of the most widely performed orthopedic procedures in the United States. It is estimated that about 170,000 THAs are performed each year in the United States, and about 300,000 worldwide.

One of the most important aspects of THA is ensuring proper alignment of the acetabular component or implant with respect to the pelvis. Specifically, studies have shown that failure to properly align the acetabular component or implant with the pelvis may lead to premature wear, propensity to dislocate and patient discomfort.

SUMMARY

The described embodiments relate to methods and systems for use in aligning a prosthesis during surgery, as well as a device for positioning a sensor.

In one broad aspect, there is provided a method for determining the orientation of a surgical tool with respect to a bone of a patient, the bone having at least three predetermined reference locations. The method includes:

defining a reference plane based on distances between the at least three predetermined reference locations;

determining a first sensing location on the bone based on the at least three predetermined reference locations;

attaching a first active sensor to the bone at the first sensing location;

positioning the surgical tool proximate the bone, the surgical tool comprising a second active sensor;

sensing movement of the bone using the first active sensor;

transmitting first information relating to movement of the bone using the first active sensor;

sensing movement of the surgical tool using the second active sensor;

transmitting second information relating to movement of the surgical tool using the second active sensor;

receiving the first and second information from the first and second active sensors; and determining a three-dimensional orientation of the surgical tool with respect to the reference plane based on the first and second information.

In another feature of that aspect, the method further includes displaying the three-dimensional orientation of the surgical tool with respect to the reference plane on a display device.

In another feature of that aspect, the bone is a pelvis. In another feature of that aspect, determining the three-dimensional orientation of the surgical tool with respect to the reference plane comprises determining an angle of abduction and an angle anteversion. In another feature of that aspect, the first active sensor is attached to the iliac crest.

In another feature of that aspect, the distances between the at least three reference predetermined locations are determined using at least one pre-operative scan.

In another feature of that aspect, at least two of the at least three predetermined reference locations are palpable bony landmarks. In another feature of that aspect, at least three predetermined reference locations are bony palpable landmarks.

In another feature of that aspect, the first active sensor is attached to the bone using a bone screw.

In another feature of that aspect, the first and second active sensors each comprise at least one accelerometer and at least one gyroscope.

In another broad aspect, there is provided a system for determining the orientation of a surgical tool with respect to a bone of a patient, the bone having at least three predetermined reference locations. The system includes:

a first active sensor, the first active sensor adapted for sensing movement of the first active sensor and transmitting first information relating to movement of the first active sensor;

a second active sensor, the second active sensor adapted for sensing movement of the second active sensor and transmitting second information relating to movement of the second active sensor;

a sensor positioning device adapted for positioning the first active sensor on the bone based on the at least three predetermined reference locations;

a surgical tool attached to the second active sensor, the surgical tool adapted for attaching a prosthetic to the bone; and a processor in communication with the first and second sensors, the processor adapted for: defining a reference plane based on distances between the at least three reference locations; receiving the first and second information; and determining a three-dimensional orientation of the surgical tool with respect to the reference plane based on the first and second information.

In another feature of that aspect, the system also includes a display device adapted for displaying the three dimensional orientation received from the processor.

In another feature of that aspect, the bone is a pelvis. In another feature of that aspect, the processor is further adapted to determine an angle of abduction and an angle of anteversion based on the three-dimensional orientation of the surgical tool with respect to the reference plane. In another feature of that aspect, the first active sensor is positioned on a portion of the iliac crest.

In another feature of that aspect, the distances between the at least three reference locations are determined from at least one pre-operative scan and input into the processor.

In another feature of that aspect, at least two of the at least three predetermined reference locations are bony palpable landmarks. In another feature of that aspect, the at least three predetermined reference locations are bony palpable landmarks.

In another feature of that aspect, the first and second active sensors each comprise at least one accelerometer and at least one gyroscope.

In another broad aspect, there is provided a device for positioning a sensor at a predetermined location on a bone of a patient, the bone having a first reference location, a second reference location, and a third reference location. The device comprises:

a shaft;

a first contact member operatively connected to the shaft, wherein the first contact member is adapted for contacting the first reference location on the bone;

a second contact member operatively connected to the shaft and spaced apart from the first contact member, wherein the second contact member is adapted for contacting the second reference location;

an arm operatively connected to the shaft, wherein the arm is movable relative to the first and second contact members;

a third contact member operatively connected to the arm, wherein the third contact member is adapted for contacting the third reference location; and a guide coupled to the arm for positioning the sensor at the predetermined location and orientation on the bone when the first contact member is in contact with the first reference location, the second contact member is in contact with the second reference location and the third contact member is in contact with the third reference location.

In another feature of that aspect, the arm is rotatable about the shaft.

In another feature of that aspect, the arm is positioned between the first and second contact elements.

In another feature of that aspect, the arm and shaft are fixedly attached and are rotatable with respect to the first and second contact members.

In another feature of that aspect, the arm is positioned at an end of the shaft.

In another feature of that aspect, the shaft is extendable. In another feature of that aspect, the shaft is a telescoping shaft.

In another feature of that aspect, the guide comprises a first portion movably connected to a second portion, wherein the first portion is movable between an open position and a closed position, wherein in the closed position, the first portion is in engagement with the second portion to position the sensor in the predetermined position, wherein, in the open position, the first portion is disengaged from the second portion to permit removal of the device after the sensor is positioned at the predetermined location.

In another feature of that aspect, the second portion is hingedly connected to the first portion.

In another feature of that aspect, the first and second portions each define a notch, wherein in the closed position, the notch in the first portion and the notch in the second portion form a screw hole.

In another feature of that aspect, the sensor is secured to the bone using a bone screw.

Further aspects and advantages of the embodiments described herein will appear from the following description taken together with the accompanying drawings.

BRIEF DESCRIPTION OF THE DRAWINGS

For a better understanding of embodiments of the systems, methods and devices described herein, and to show more clearly how they may be carried into effect, reference will be made, by way of example, to the accompanying drawings in which.

Figure 1:
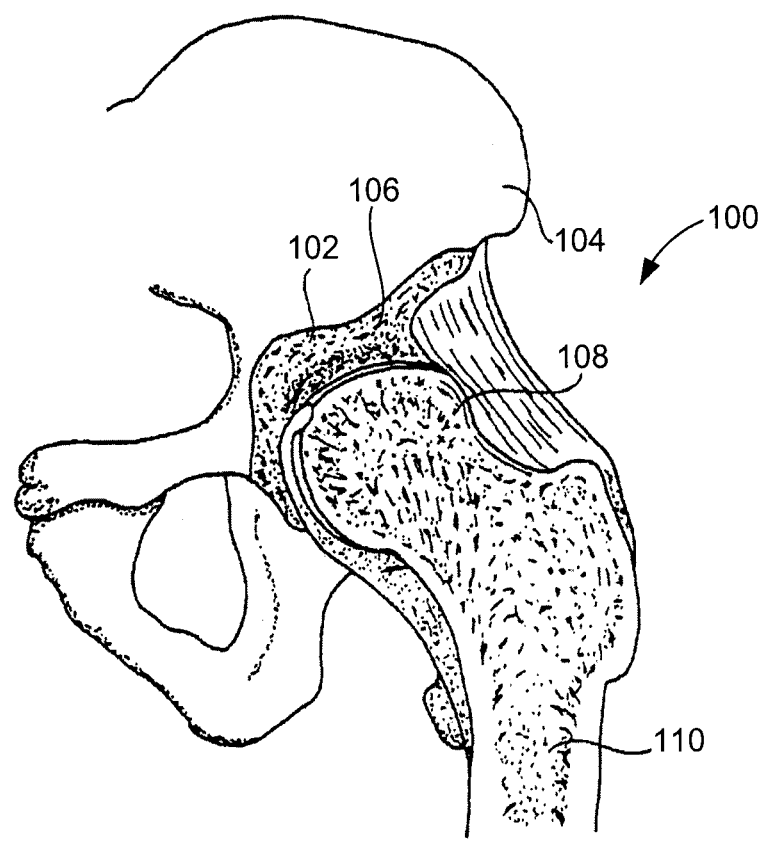
FIG. 1 is a front view of a normal hip joint.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The described embodiments relate to methods and systems for aligning a prosthesis during surgery. The exemplary methods and systems involve determining the three-dimensional orientation of the prosthesis with respect to a body part during surgery to assist a surgeon in properly aligning the prosthesis with the body part. In one embodiment, the three-dimensional orientation of the prosthesis with respect to the body party is determined using two active sensors. One active sensor is attached to the body part and actively monitors movement of the body part. The other active sensor is attached to the surgical tool used to insert the prosthesis and actively monitors movement of the surgical tool (and thus the prosthesis). The movement information detected by the sensors is then used to determine the three dimensional orientations of the prosthesis and the body part with respect to each other. In one embodiment, the active sensors are inertial sensors.

For ease of explanation, the methods and systems will be described in reference to aligning an acetabular implant during total hip arthroplasty (THA) or total hip replacement (THR). However, it will be evident to a person of skill in the art that the methods and systems described herein may be applied to any other surgical procedure where a prosthesis is implanted, such as, for example, knee replacement surgery.

Before proceeding to a detailed description of the embodiments of methods and systems for aligning an acetabular component or implant, a brief description of total hip replacement (THR) or total hip arthroplasty (THA) will be provided with reference to FIGS. 1-4.

Reference is first made to FIG. 1, in which a normal human hip joint 100 is illustrated. As can be seen from FIG. 1, the hip joint 100 includes a socket 102, referred to as the acetabulum, in the pelvic bone 104 which is lined with acetabular cartilage 106. In a healthy individual, the femoral head 108 at the upper end of the femur 110 is received in the acetabulum 102.

Figure 2:
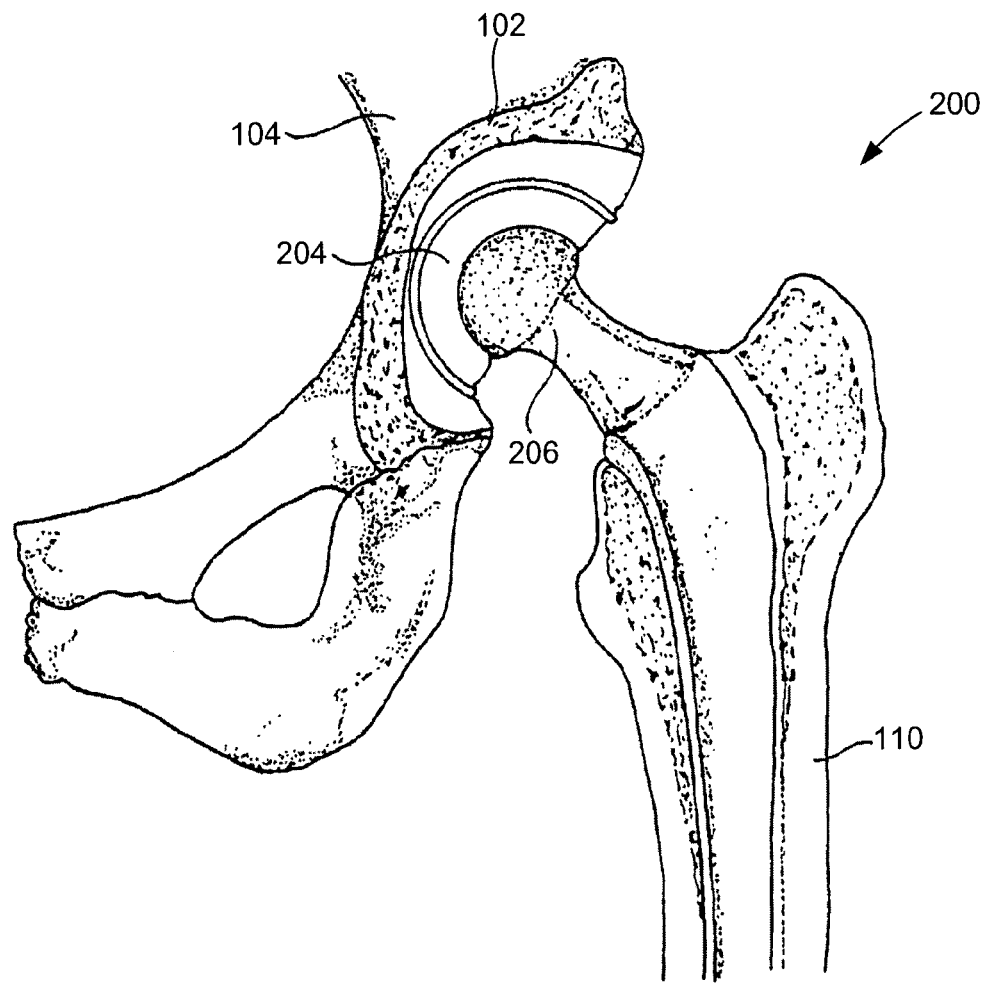
FIG. 2 is a front view of a hip joint after total hip arthroplasty.

Reference is now made to FIG. 2, in which a human hip joint 200 after THR or THA surgery is illustrated. During THR or THA, the acetabulum 102 is reamed out (i.e. the remaining acetabular cartilage 106 is removed), and an acetabular component or implant 204 is attached to the acetabulum 102. The femoral head 108 (shown in FIG. 1) of the femur 110 is also removed. Specifically, the femur 110 is opened out by a teeth dilator (not shown), and a ball and socket component 206, referred to as the femoral component, is inserted into the opened-out femur 110.

One of the most important aspects of THA is ensuring proper alignment of the acetabular component or implant with respect to the pelvis. Specifically, studies have shown that failure to properly align the acetabular component or implant with the pelvis may lead to premature wear, propensity to dislocate and patient discomfort.

Figure 3:
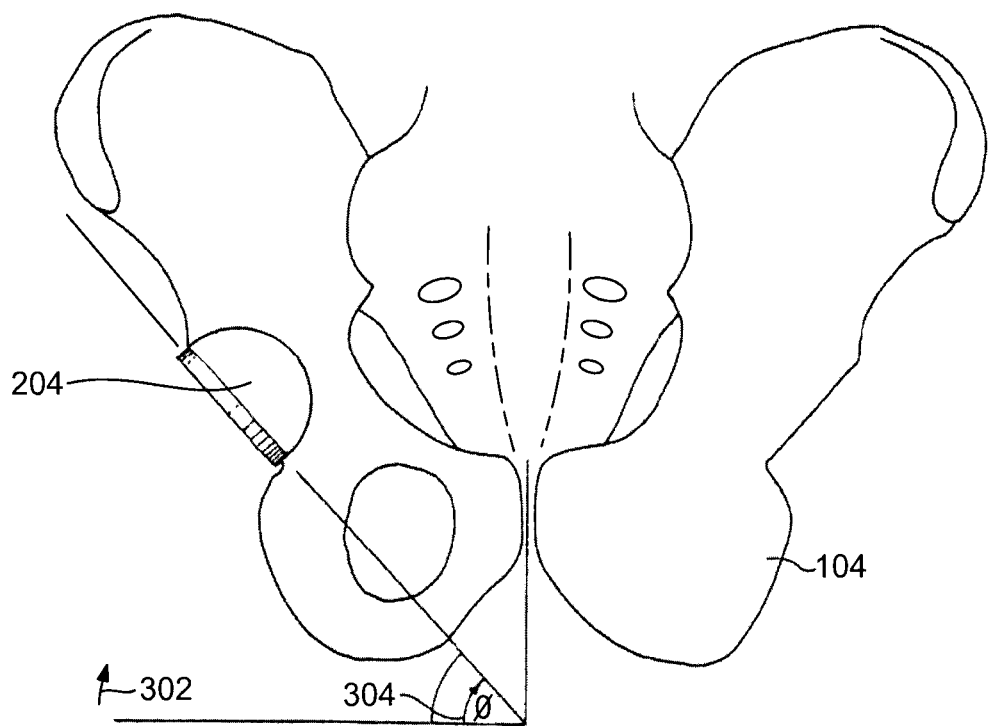
FIG. 3 is front view of a pelvis showing the angle of abduction.
Figure 4:
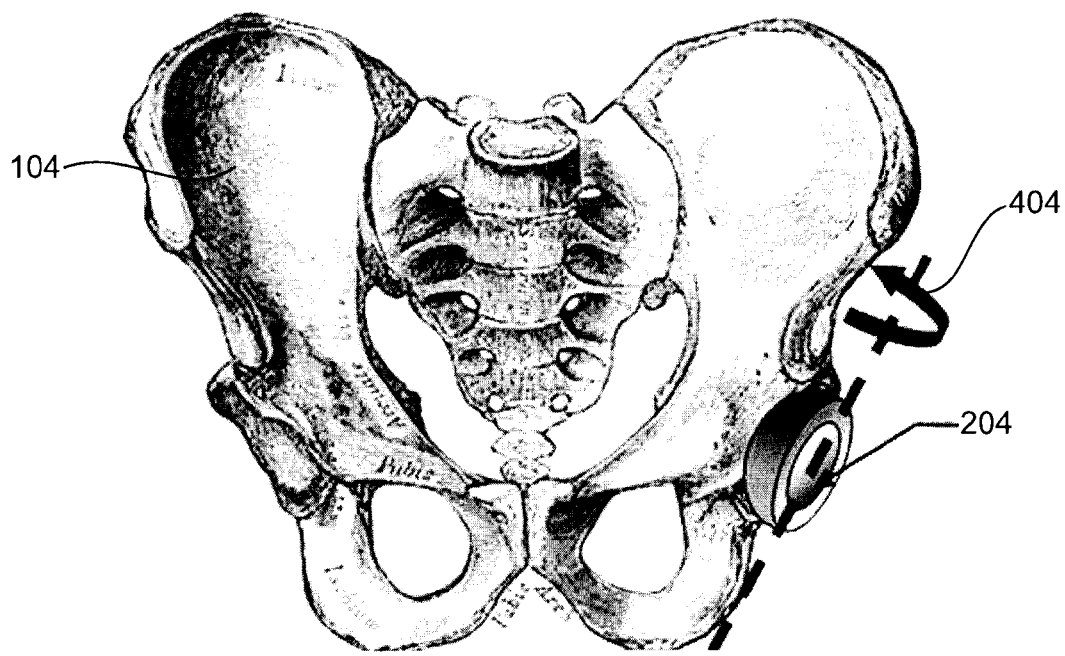
FIG. 4 is a front view of a pelvis showing the angle of anteversion.

The precise orientation of the acetabular component or implant 204 is defined by angles of abduction and anteversion. Reference is now made to FIGS. 3 and 4, which illustrate the angles of abduction and anteversion respectively. FIG. 3 is a front view of the pelvic bone 104. The direction of abduction is indicated by arrow 302, and the angle of abduction is indicated by angle 304. In general, abduction relates to the sideways pivoting of the acetabular component or implant 204 in the acetabulum 102. FIG. 4 is also a front view of the pelvic bone 104. The angle of anteversion is indicated by angle 404. In general, anteversion relates to rotation of the acetabular component or implant 204 about its axis towards the front of the body.

Studies have shown that for a typical patient, the angle of abduction is ideally between 42° and 48°, and the angle of anteversion is ideally between 12° and 18°.

Figure 5:
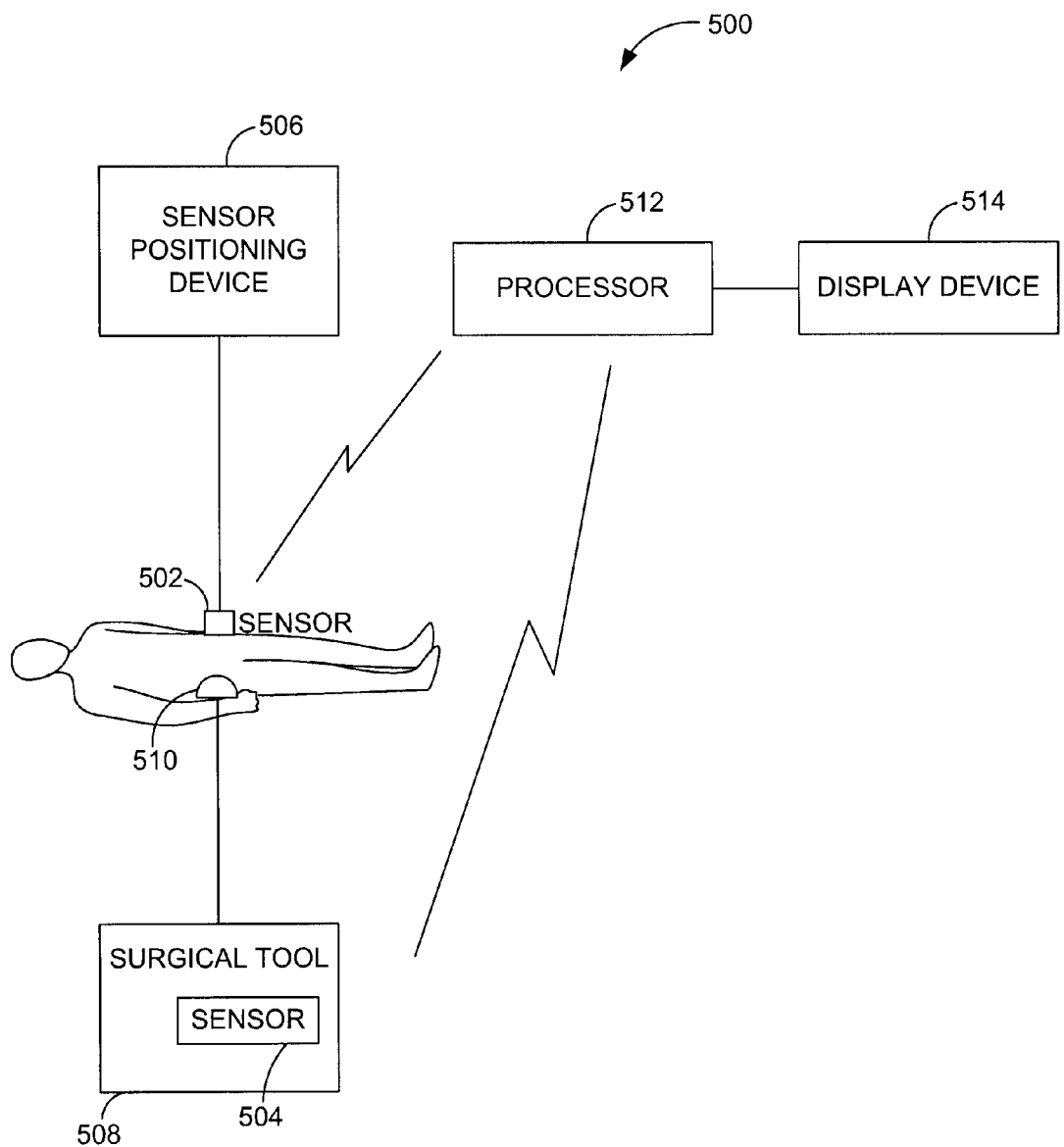
FIG. 5 is a block diagram of a system for aligning an acetabular implant during total hip arthroplasty in accordance with at least one embodiment.

Reference is now made to FIG. 5, in which a system 500 for aligning an acetabular component or implant with the pelvis during THA or THR in accordance with an embodiment of the present invention is illustrated. The system 500 includes first and second active sensors 502 and 504, a sensor positioning device 506, a surgical tool 508, the acetabular component or implant 510, a processor 512 and a display device 514.

The first and second active sensors 502 and 504 are designed to actively sense movement of the active sensor 502 or 504 in space, preferably in real-time, and the first and second active sensors 502, 504 transmit the sensed movement information to a remote device, such as the processor 512. The movement information may be transmitted to the remote device in any suitable fashion, such as via Ethernet or other wired medium, or wirelessly.

In some embodiments, the first and second active sensors 502 and 504 are inertial sensors that use a combination of accelerometers and gyroscopes to detect the inertial movement of the sensor. For example, each active sensor 502 and 504 may have three accelerometers and three gyroscopes. In these embodiments, the active sensors 502 and 504 typically sense and transmit information related to the angular acceleration and velocity of the active sensor 502 or 504. In some embodiments, the active sensors 502 and 504 may also include a magnetometer for measuring the magnetic field surrounding the sensor. In still further embodiments, the active sensors 502 and 504 may also include a local optical device, such as a camera, to monitor a physical marker remote to the sensor. Inertial sensors are typically preferred over optical sensors because they do not have the same line of sight issues that optical sensors have.

Typically, the first active sensor 502 is positioned on the pelvis of the patient in a predetermined position and orientation with respect to the pelvis, and the second active sensor 504 is placed on the surgical tool 508 used to insert/attach the acetabular component or implant 510. The movement information collected by the first and second active sensors 502 and 504 can then be used to determine the three-dimensional orientation of the acetabular component or implant 510 with respect the patient's pelvis. In some embodiments, such as embodiments where the active sensors 502 and 504 are inertial sensors, the first and second active sensors 502 and 504 are preferably initialized to have a predetermined orientation with respect to each other prior to beginning the surgery in order to accurately determine the three-dimensional orientation of the acetabular component or implant 510 with respect to the patient's pelvis during surgery.

The sensor positioning device 506 is used to position the first active sensor 502 at a predetermined location on the pelvis of the patient. The predetermined location is selected to have a predefined relationship to a pelvic reference plane defined by three or more pelvic reference locations. By placing the first active sensor 502 on the pelvis in a predetermined position and orientation to the pelvic reference plane, changes in orientation to the pelvic reference plane can be tracked by changes in orientation of the first active sensor 502.

The pelvic reference locations are typically anatomical landmarks on the pelvis. For example, these locations may include bony palpable landmarks, such as the right and left anterior superior iliac spine (ASIS) points, or non-palpable locations, such as the two pubic tubercles or the mid-point between the two pubic tubercles, or both. It will be evident, however, to a person of skill in the art that any other suitable anatomical landmarks may also be used as pelvic reference locations.

The sensor positioning device 506 mechanically establishes the pelvic reference plane by lining up mechanical features of the sensor positioning device 506 with the pelvic reference locations. Preferably, the sensor positioning device 506 has three contact members that are used to contact three pelvic reference locations simultaneously. Once the sensor positioning device 506 has been brought into contact with the pelvic reference locations, the sensor positioning device 506 is used to position the first active sensor 502 in a predetermined relationship to the pelvic reference plane. Once positioned, the first active sensor 502 is attached to the pelvis via any suitable technique. For example, the first active sensor 502 may be attached to the pelvis using a bone screw, a biocompatible adhesive, or a clamp.

Upon attaching the first active sensor 502 to the pelvis, the sensor positioning device 506 may be removed from the patient's body.

Two exemplary sensor positioning devices will be described in reference to FIGS. 6A to 8C.

The surgical tool 508 is used to insert the acetabular component or implant 510 into the acetabulum of the patient. The second active sensor 504 is attached or mounted to the surgical tool 508 in a predetermined position and orientation with respect to the acetabular component or implant 510. In this manner, changes in orientation to the acetabular component or implant 510 can be tracked by changes in orientation of the second active sensor 504 An exemplary surgical tool 508 will be described in reference to FIG. 9.

The processor 512 is in communication with the first and second active sensors 502 and 504 and the display device 514. The processor 512 is configured to perform the following: (1) define the pelvic reference plane based on distances between the three or more pelvic reference locations; (2) receive the transmitted movement information from the first and second active sensors 502 and 504; (3) calculate the three-dimensional orientation of the second active sensor 504 (and thus the surgical tool 108) relative to the pelvic reference plane based on the movement information received from the first and second active sensors 502 and 504; and (4) output the three-dimensional orientation information to the display device 514 to be displayed to the surgeon.

The processor 512 defines the pelvic reference plane based on inputted distances between the three or more pelvic reference locations. The pelvic reference plane is then used to relate the relative orientation of the first and second active sensors 502 and 504 to measures of interest (i.e. angles of abduction and anteversion). An exemplary method for defining the pelvic reference plane using three pelvic reference locations will be described in reference to FIGS. 10 and 11.

In some embodiments, the distances between the three or more pelvic reference locations are manually measured using one or more pre-operative scans (i.e. x-rays) and then input into the processor 512. However, it will be evident to those of skill in the art that the distances may be determined in any other suitable fashion. For example, the distances may be measured on the patient using a measuring device such as a tape measure. In some embodiments, the distances may be manually input into the processor using any suitable input device, such as a keyboard, touch screen or mouse. However, it will be evident to those of skill in the art that the distances may be input into the processor 512 in any other suitable fashion. The distances are typically measured and input into the processor 512 prior to surgery.

During surgery, the processor 512 receives the transmitted movement information from the first and second active sensors 502 and 504. As described above, the transmitted movement information may be transmitted from the first and second active sensors 502 and 504 through a wired medium or wirelessly. The movement information may be transmitted by the first and second active sensors 502 and 504 using a standard communication protocol, such as RS-232 or USB, or any other suitable communication protocol.

The processor 512 typically performs pre-processing on the received information prior to determining the three dimensional orientation of the acetabular component or implant with respect to the pelvis, and more specifically with respect to the acetabulum. Pre-processing may include performing filtering or conditioning or both. Typically the type of filtering performed by the processor 512 is based on the type of active sensors employed. For example, gyroscopic sensors are subject to drift; therefore, where gyroscopic sensors are used, a high pass filter may be employed to compensate for the drift. The processor 512 may also condition the received movement information for further processing. For example, the processor 512 may adjust the received movement information to account for temperature or other factors. The pre-processing may be implemented by the processor 512 in hardware (i.e. a field programmable gate array (FPGA)) or in software. In some embodiments, additional or alternate pre-processing may be performed by the active sensors 502 and 504 prior to transmission of the movement information.

Once the pre-processing is complete, the processor 512 processes the received movement information to determine the three-dimensional orientation of the acetabular component or implant 510 with respect to the pelvis (and more specifically determines angles of abduction and anteversion). Processing of the received movement information typically involves: (i) converting the received movement information into a format suitable for performing orientation calculations; and (ii) comparing the converted movement information from the first and second active sensors to determine the three dimensional orientation of the acetabular component or implant 510 with respect to the pelvis (and more specifically determines angles of abduction and anteversion).

Converting the received movement information into a format suitable for performing orientation calculations preferably includes converting the received movement information into rotational matrices, quaternions, or other suitable formats. The specific format is typically based on the type of active sensors used in the system 500.

Once the received movement information has been converted into a suitable format, the processor 512 determines the orientation of the two active sensors 502 and 504. The processor 512 then uses the orientation of the first active sensor 502 to determine the orientation of the pelvic reference plane and thus the pelvis. Specifically, since the first active sensor 502 is in a predetermined position and orientation with respect to the pelvic reference plane, any changes in orientation to the first active sensor 502 can be translated into changes in orientation to the pelvic reference plane, and thus the pelvis. An exemplary method for translating the orientation first active sensor to the orientation of the pelvic reference plane will be described in reference to FIG. 12. The processor 512 similarly uses the orientation of the second active sensor 504 to determine the orientation of the surgical tool 508 and thus the acetabular component or insert 510. Specifically, since the second active sensor 504 has a predetermined position and orientation with respect to the surgical tool 508, any changes in orientation to the second active sensor 504 can be translated into changes in orientation to the surgical tool 508, and thus the acetabular component or insert 510.

Once the orientations of the pelvis and the acetabular component or implant 510 have been determined, the processor 512 compares the orientations to determine the three dimensional orientation of the acetabular component or implant 510 with respect to the pelvis. Specifically, any changes in orientation to either sensor can be used to determine changes in orientation of one sensor (and its corresponding device or body party) with respect to the other. In some embodiments, such as embodiments where the active sensors 502 and 504 are inertial sensors, the first and second active sensors 502 and 504 are preferably initialized to have a predetermined orientation with respect to each other prior to beginning the surgery in order to accurately determine the three-dimensional orientation of the acetabular component or implant 510 with respect to the patient's pelvis during surgery. This is typically accomplished through an initialization process. In one embodiment, determining the three dimensional orientation of the acetabular component or implant 510 with respect to the pelvis includes determining angles of abduction and anteversion.

Once the processor 512 has determined the orientation of the acetabular component or implant 510 with respect to the pelvis, the processor 512 outputs this information to the display device 514 to be displayed to the surgeon.

The processor 512 may also store any of the data it processes in an internal or external memory unit (not shown). For example, the processor 512 may store the movement data it receives from the first and second active sensors 502 and 504, or the generated angles of abduction and anteversion, or both. The processor 512 may be implemented in hardware or software.

The display device 514 receives information from the processor 512 setting out the orientation of the acetabular component or implant 510 with respect to the pelvis and displays the information in a usable format. The display device 514 may be any suitable display such as a digital display or a graphical display. Where the orientation information includes the angles of abduction and anteversion, the display device 514 may display these angles. This allows the surgeon to adjust the position of the surgical tool 508, and thus the acetabular implant or component 510, until desired angles of abduction and anteversion are achieved.

Reference is now made to FIGS. 6A to 6D, which illustrate a sensor positioning device 600 in accordance with a first embodiment. As described above, the sensor positioning device 600 is used to position the first active sensor 502 on the pelvis in a predetermined location and orientation with respect to the pelvic reference plane. The sensor positioning device 600 includes a shaft 602 to which two link members 614, 616 and an arm 608 are connected. First and second contact members 604, 606 are coupled to distal ends of link members 614, 616, respectively. A third contact member 610 is coupled to one end of the arm 608 and a guide 612 is coupled to another end of the arm 608.

The first, second and third contact members 604, 606 and 610 are each designed to contact one of the pelvic reference locations (i.e. right and left ASIS). As described above, the pelvic reference locations can include bony palpable landmarks, such as the right and left ASIS points, or non-palpable locations, such as a point in the pubic region, or both. In the embodiment shown in FIG. 6, the three pelvic reference locations include two bony palpable landmarks—the right and left ASIS points—and one non-palpable point—a point in the pubic region. In this embodiment, the first and second contact members 604 and 606 are designed to come into contact with the two ASISs and the third contact member 610 is designed to come into contact with the location in the pubic region. In one embodiment, the first and second contact members 604 and 606 are each in the shape of a flange having a depression (not shown) therein in which the corresponding ASIS point is received.

The shaft 602 preferably spans the front of the patient's pelvis. In some embodiments, the shaft 602 is adjustable to accommodate patients with differing pelvic sizes. For example, in an alternative embodiment (not shown), the shaft 602 may be a telescoping shaft.

The link members 614 and 616 may also be adjustable to account for patients of different sizes. For example, link members 614 and 616 may be threaded shafts that are received in complementary-threaded holes in the shaft 602. In this embodiment, screwing or unscrewing the link members 614 and 616 into or out of the corresponding holes in the shaft 602 adjusts the length of the link members 614 and 616.

The arm 608 is connected to the shaft 602 and is used to: (i) bring the third contact member 610 into contact with the third pelvic reference location; and (ii) align the guide 612 with a point on the pelvis that has a predetermined relationship to the pelvic reference plane. Preferably, a block 615 is connected to the arm 608. The block 615 has a bore 617 therethrough which receives the shaft 602 to permits the arm 608 to rotate about the shaft 602. After the first and second contact members 604 and 606 are brought into contact with the first and second pelvic reference locations (right and left ASIS points) respectively, the arm 608 is rotated about the shaft 602 to bring the third contact member 610 into contact with the third pelvic reference location (the predetermined point in the pubic region). This in turn brings the guide 612 into alignment with a location on the pelvis that has a predetermined relationship to the pelvic reference plane. Once the guide 612 is in place, the guide 612 is used to attach the first active sensor 502 to the predetermined location on the pelvis.

In the embodiment shown in FIG. 6, the arm 608 includes three portions: a contact portion 618, an intermediate portion 620, and a guide portion 622. Preferably, the contact portion 618 is positioned on the shaft 602 between the first and second link members 614 and 616 (and thus the first and second contact members 604 and 606) and extends a predetermined distance down from the shaft 602. The third contact member 610 is located at a distal end of the contact portion 618. In the embodiment shown in FIG. 6, the third contact member 610 is a point that is designed to be brought into contact with the third pelvic reference location.

As described above, in this embodiment, the third pelvic reference location is a non-palpable reference location, namely a point near the pubic region. Since in this embodiment the third pelvic reference location is not easily locatable by touch or eye, the third pelvic reference location is typically marked on the skin of the patient prior to surgery, and the third contact member 610 is brought into contact with the marker on the patient's skin.

The intermediate portion 620 of the arm 608 connects the contact portion 618 and the guide portion 622 in a predetermined relationship. The intermediate portion 620 preferably extends along the shaft 602 and has a fixed length.

Figure 6A:
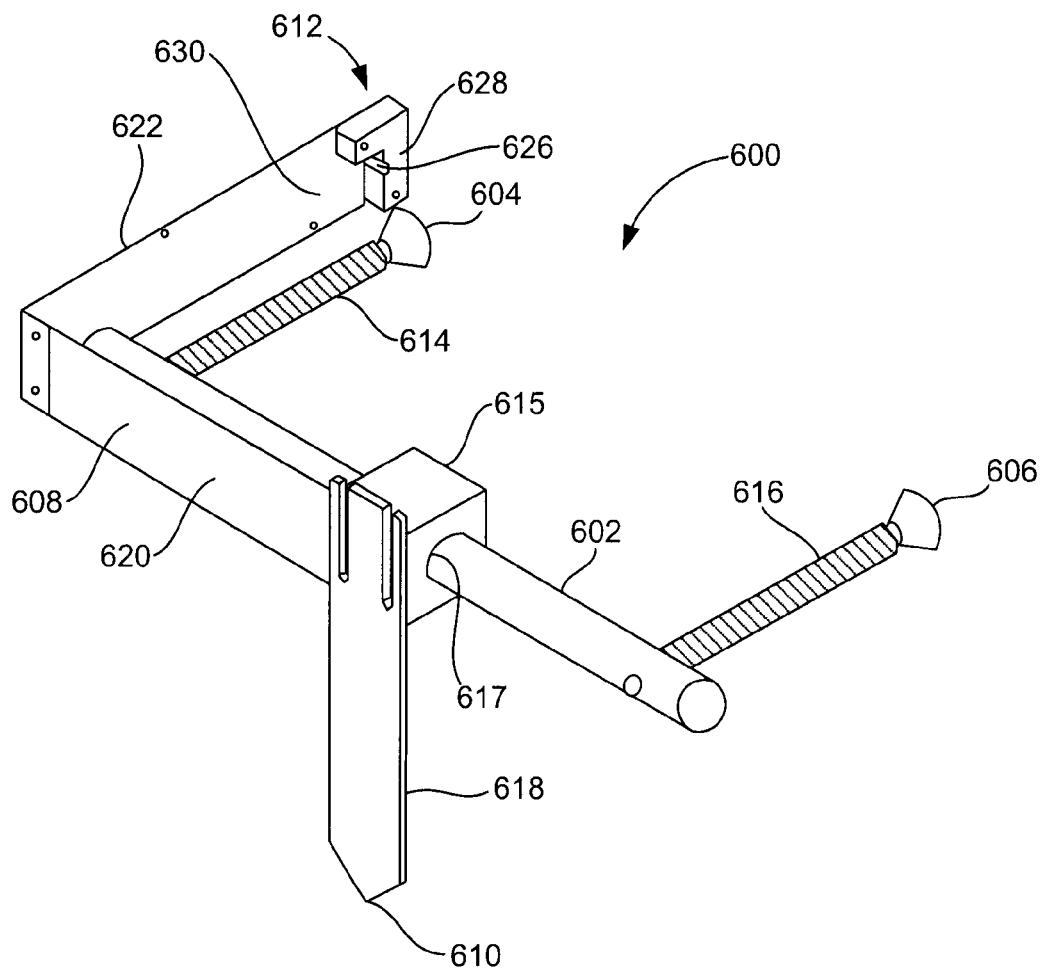
FIG. 6A is an isometric view of a sensor positioning device in accordance with a first embodiment.
Figure 6B:
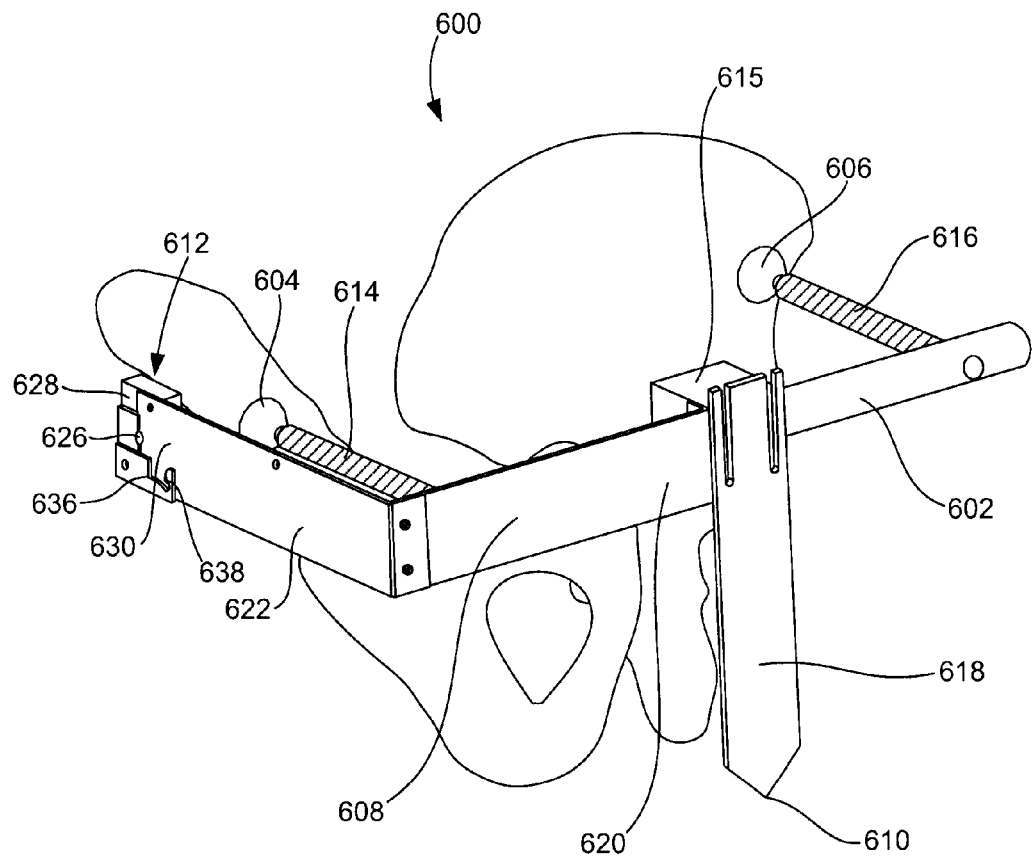
FIG. 6B is an isometric view of the sensor positioning device of FIG. 6A in contact with the pelvis with the first portion of the guide in the closed position.
Figure 6C:
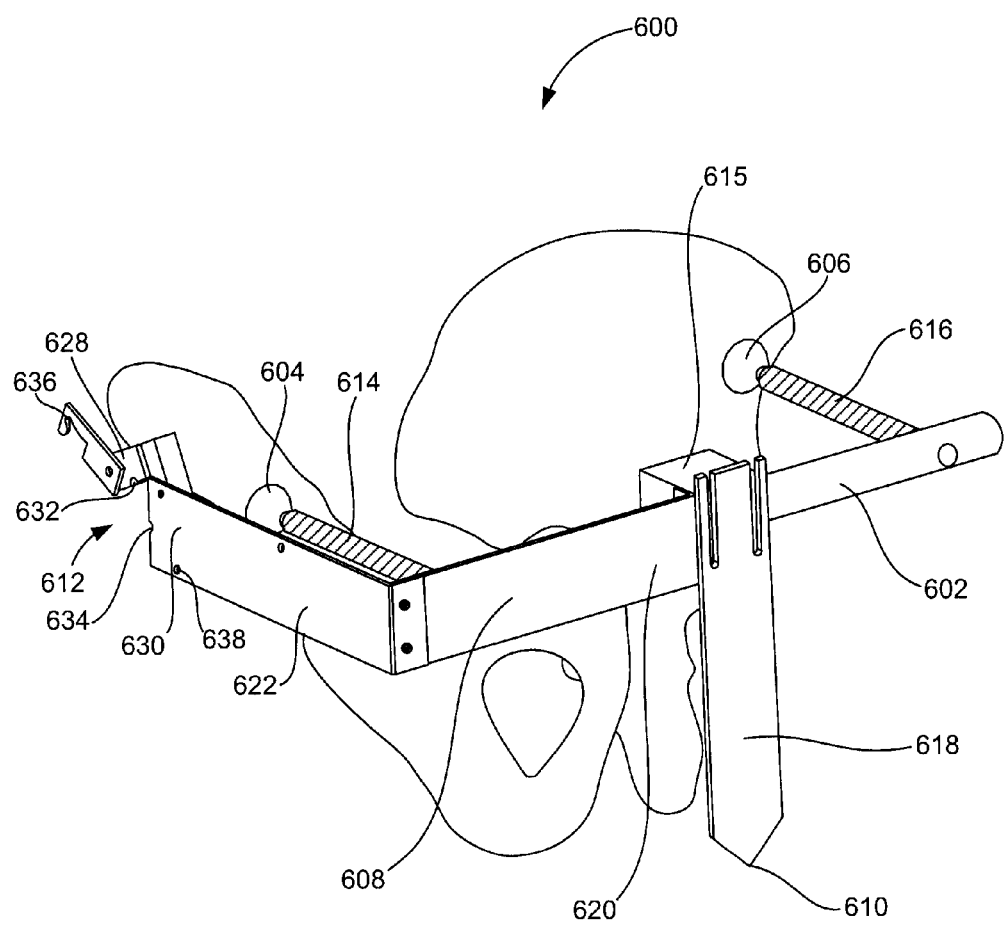
FIG. 6C is an isometric view of the sensor positioning device of FIG. 6A in contact with the pelvis with the first portion of the guide in the open position.
Figure 6D:
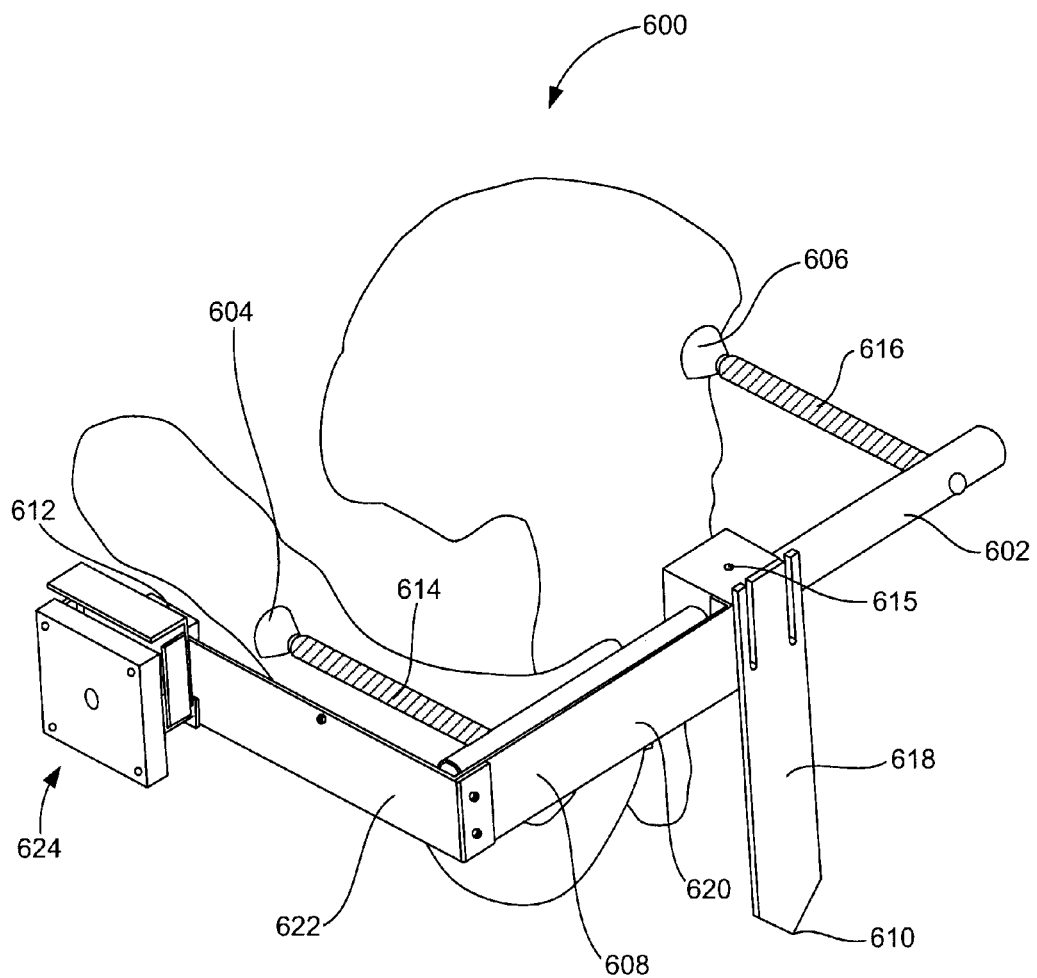
FIG. 6D is an isometric view of the sensor positioning device of FIG. 6A in contact with the pelvis with a sensor mount inserted in the guide.

One end of the guide portion 622 is secured to the intermediate portion 620 of the arm 608 and the guide 612 is secured to the other end of the guide portion 622. The guide portion 622 preferably extends towards the patient's pelvis and is perpendicular to the intermediate portion 620. All three portions of the arm 608—the contact portion 618, the intermediate portion 620 and the guide portion 622—work together to position the guide 612 in alignment with a predetermined location on the pelvis. Once the guide 612 is in position, the first active sensor 502 is inserted into the guide 612 and attached to the pelvis at the predetermined location. In some embodiments, the first active sensor 502 is removably attached to a sensor mount 624 and it is the sensor mount 624 that is inserted into the guide 612 and used to attach the first active sensor 502 to the pelvis. FIG. 6D illustrates the sensor positioning device 600 with an exemplary sensor mount 624 inserted in the guide 612.

The specific configuration of the guide 612 is dependent on the method used to attach the first active sensor 502 to the pelvis. For example, where the first active sensor 502 is attached to the pelvis using a bone screw (not shown), the guide 612 may be a hole 626 that guides the bone screw to the predetermined position on the pelvis. In such an embodiment, the guide 612 includes a movable first portion 628 and a second portion 630. The first portion 628 has a first notch 632 that preferably forms half of the hole, and the second portion 630 has a second notch 634 that preferably forms the other half of the hole 626. When the first and second portions 628 and 630 are in the closed position, the two notches 632 and 634 are aligned to form the hole 626.

The first portion 628 is hinged to the second portion 630 to permit the first portion 628 to move between a closed position and an open position. When the first portion 628 is in the closed position the notches 632 and 634 of the first and second portions 628 and 630 form the hole 626 which guides the bone screw to the predetermined position on the pelvis. When the first portion 628 is moved to the open position, the notch 632 of the first portion 628 is spaced apart from the notch 634 of the second portion 630 so that the sensor positioning device 600 can be moved away from the patient after the first active sensor 502 has been attached to the pelvis. FIG. 6B illustrates the first portion 628 in the closed position, and FIG. 6C illustrates the first portion 628 in the open position.

In some embodiments, the first portion 628 includes a latch 636 that interacts with a screw 638 (or similar device) on the second portion 630 to secure the first portion 628 in the closed position until the latch 636 is manually released from the screw 638. It will be understood by those skilled in the art that the first portion 628 can be secured to the second portion 630 in any other suitable fashion.

In some embodiments, the first active sensor 502 has an orientation marker that can be manually aligned with an orientation marker on the guide 612 to ensure that the first active sensor 502 has a predefined orientation with respect to the sensor positioning device 600. In one embodiment, the first active sensor 502 has an arrow that is manually aligned with an arrow on the guide 612. In another embodiment, the guide 612 includes a keyed slot which forces the bone screw to be inserted in the guide 612 in a specific orientation.

Figure 7:
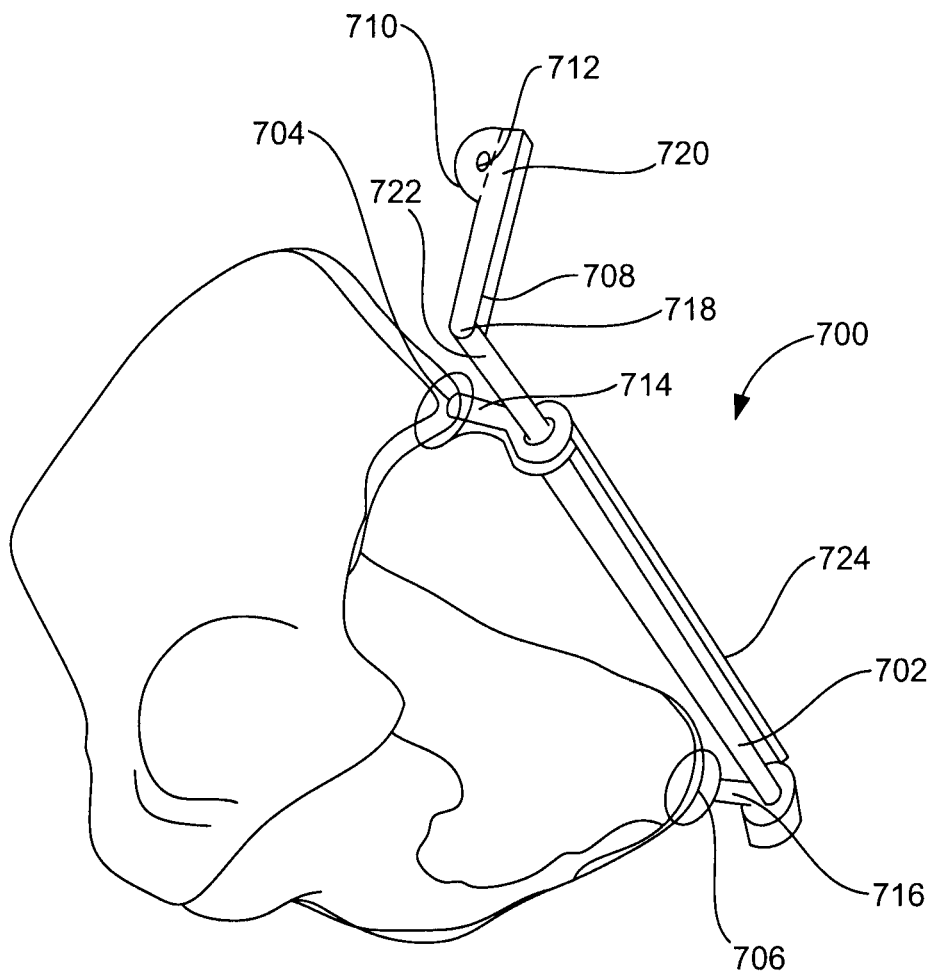
FIG. 7 is an isometric view of sensor positioning device in contact with the pelvis, in accordance with a second embodiment.

Reference is now made to FIG. 7, which illustrates a sensor positioning device 700 in accordance with a second embodiment. Similar to the sensor positioning device 600 of FIG. 6, the sensor positioning device 700 of FIG. 7 is used to position the first active sensor 502 on the pelvis in a predetermined position and orientation with respect to the pelvic reference plane. The main difference between the sensor positioning device 600 of FIG. 6, and the sensor positioning device 700 of FIG. 7, is the pelvic reference locations used to define the pelvic reference plane. The sensor positioning device 600 of FIGS. 6A to 6D uses the two ASIS points and a non-palpable point in the pubic region as the three pelvic reference locations. In contrast, the sensor positioning device 700 of FIG. 7 uses the two ASIS points and a palpable point on the iliac crest as the three pelvic reference points. One advantage of using the palpable point on the iliac crest as opposed to the non-palpable point in the pelvic region is that because the point on the iliac crest is palpable it can be located during surgery without the aid of a marker. Thus, there is no need to mark the point on the patient prior to surgery. In addition, by using a palpable bony landmark instead of a skin or surface marker, the accuracy of the system 500 may be improved. Specifically, there is less variability in the third pelvic reference location.

Similar to the sensor positioning device 600 of FIG. 6, the sensor positioning devices 700 of FIG. 7 includes a shaft 702, a first contact member 704, a second contact member 706, an arm 708, a third contact member 710 and a guide 712. These components generally perform the same functions as the corresponding components of the sensor positioning device 600 of FIG. 6, but they have a slightly different configuration to accommodate the change in the third pelvic reference location.

The first, second and third contact members 704, 706 and 710 are designed to contact the first, second, and third pelvic reference locations respectively. As described above, in this embodiment, the first, second, and third pelvic reference locations are the right ASIS, left ASIS, and a point on the iliac crest. Accordingly, the first and second contact members 704 and 706 are designed to come into contact with the two ASISs. In one embodiment, the first and second contact members 704 and 706 are in the shape of a flange having a depression therein in which the corresponding ASIS point is received.

The shaft 702 preferably spans the front of the patient's pelvis and connects the first and second contact members 704 and 706. In some embodiments, the shaft 702 is adjustable to accommodate patients with differing pelvic sizes. For example, in one embodiment, the shaft 702 may be a telescoping shaft (not shown).

The first and second contact members 704 and 706 are connected to the shaft 702 via first and second link members 714 and 716, respectively, that extend away from the patient's body. Each of the first and second link members 714 and 716 typically have a hole or aperture to receive the shaft 702 so that the shaft 702 can be rotated with respect to the first and second link members 714 and 716 (and thus first and second contact members 704 and 706). In this embodiment, the first and second link members 714 and 716 have a fixed length. In other embodiments, the first and second link members 714 and 716 may have an adjustable length (not shown) to account for different-sized patients. In some embodiments, the sensor positioning device 700 may also include a bar 724 that connects the first and second link members 714 and 716 to ensure that the first and second link members 714 and 716 maintain a fixed relationship and orientation irrespective of the position or rotation of the shaft 702.

The arm 708 is used to (i) position the third contact member 710 in contact with the third pelvic reference location (i.e. a predetermined point on the iliac crest); and (ii) align the guide 712 with the predetermined position on the pelvis for attaching the first active sensor 502. Specifically, once all of the contact members 704, 706 and 710 have been brought into contact with their respective pelvic reference locations, the arm 708 takes the pelvic reference plane and translates it linearly and rotationally to a location on the pelvis.

The arm 708 has first and second ends 718 and 720. The first end 718 of the arm 708 is secured to a first end 722 of the shaft 702, and the second distal end 720 of the arm 708 is connected to the third contact member 710 and the guide 712. In contrast to the arm 608 of the sensor positioning device 600 of FIGS. 6A to 6D which is rotatable about the shaft 602, the arm 708 of the sensor positioning device 700 of FIG. 7 is fixed to the shaft 702 so that the shaft 702 and the arm 708 are together rotatable with respect to the first and second link members 714 and 716.

Once the first and second contact members 704 and 706 have manually been brought into contact with the first and second pelvic reference locations (e.g. the right and left ASISs), the operator manually rotates the arm 708 (and thus the shaft 702) to bring the third contact member 710 into contact with the third pelvic reference location (e.g. a point on the iliac crest). This in turn brings the guide 712 into alignment with the predetermined position for the first active sensor 502. The operator then inserts the first active sensor 502 into the guide 712 and attaches the first active sensor 502 to the pelvis in the predetermined position.

In some embodiments, the first active sensor 502 has an orientation marker that can be manually aligned with an orientation marker on the guide 712 to ensure that not only is the first active sensor 502 in the correct position with respect to the pelvic reference plane, but it has a predefined orientation with respect to the pelvic reference plane. In one embodiment, the first active sensor 502 has an arrow that is manually aligned with an arrow on the guide 712.

An exemplary arm 708, including the third contact member 710 and the guide 712, will be described in detail in reference to FIGS. 8A to 8C.

Figure 8A:
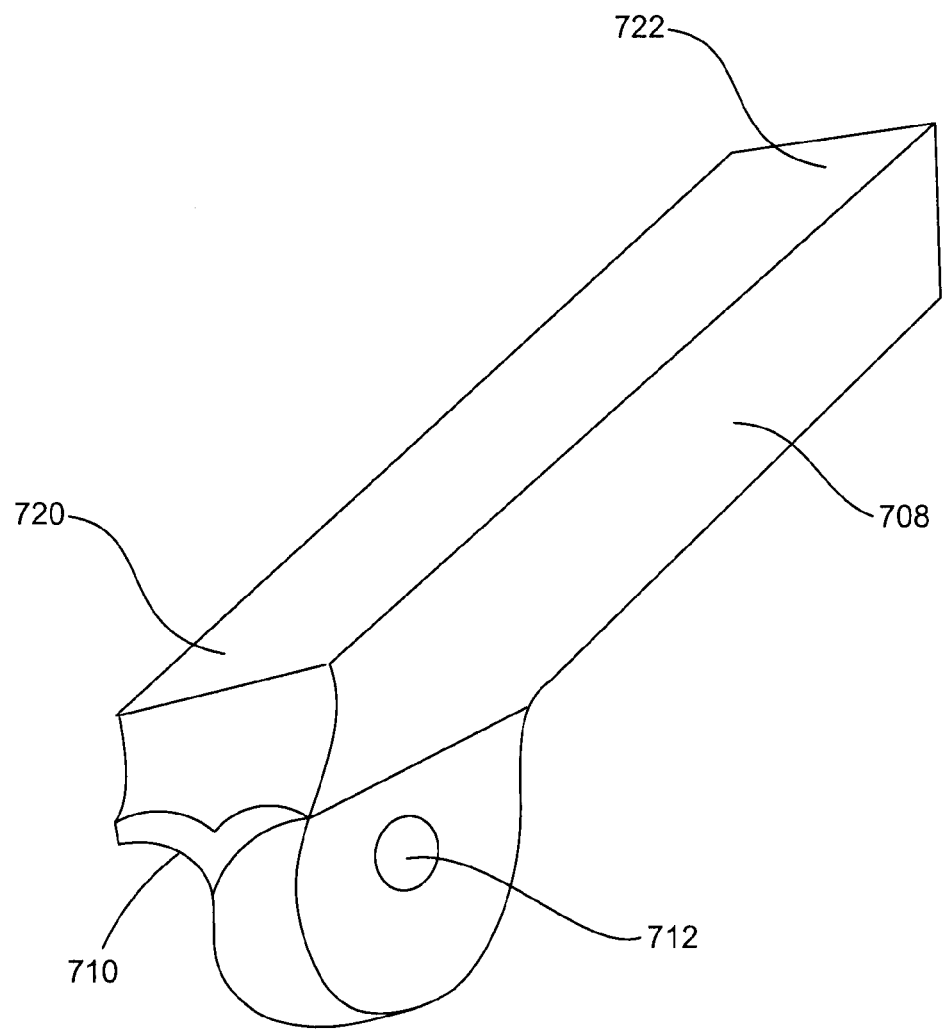
FIG. 8A is an isometric view of the arm of the sensor positioning device of FIG. 7.
Figure 8B:
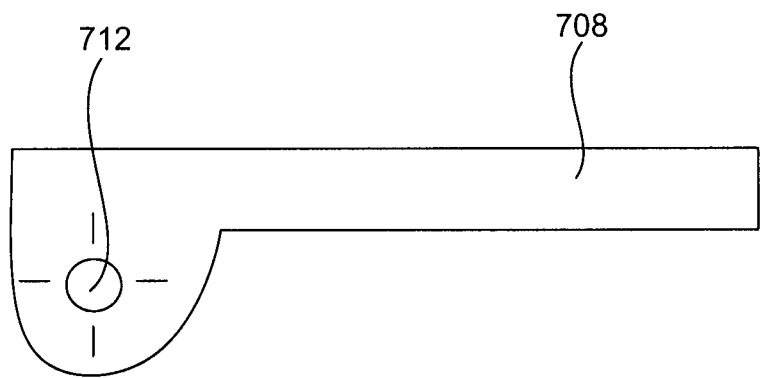
FIG. 8B is a side view of the arm of the sensor positioning device of FIG. 7.
Figure 8C:
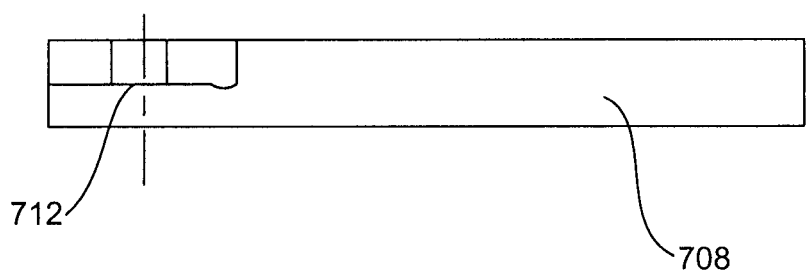
FIG. 8C is a bottom view of the arm of the sensor positioning device of FIG. 7.

Reference is now made to FIGS. 8A to 8C, which illustrate an isometric view, a top view, and a side cross-sectional view respectively of the arm 708 of the sensor positioning device 700 of FIG. 7. As described above, the arm 708 has first and second ends 718 and 720. The first end 718 of the arm 708 is connected to a first end 722 of the shaft 702, and the second end 720 of the arm 708 is connected to the third contact member 710 and the guide 712.

In the embodiment shown in FIGS. 8A to 8C, the third contact member 710 is a cut-out in the second end 720 of the arm 708 that is shaped to snugly fit against a predetermined portion of the iliac crest when the arm 708 is brought into contact with the iliac crest.

The specific configuration of the guide 712 is dependent on the method used to attach the first active sensor 502 to the pelvis. For example, where the first active sensor 502 is attached to the pelvis using a bone screw, the guide 712 may be a hole or aperture that guides the bone screw to the predetermined position on the pelvis. In such an embodiment, the guide 712 is typically divided into two portions that together form the hole or aperture. Typically, one portion is hinged to the other portion so that it is moveable with respect to the other portion. In this manner, after the first active sensor 502 has been attached to the pelvis, the movable part can be displaced so that the sensor positioning device 700 can be moved away from the patient. Preferably, the guide 712 has a similar structure and operation as guide 612 described in reference to FIGS. 6A to 6D.

Figure 9:
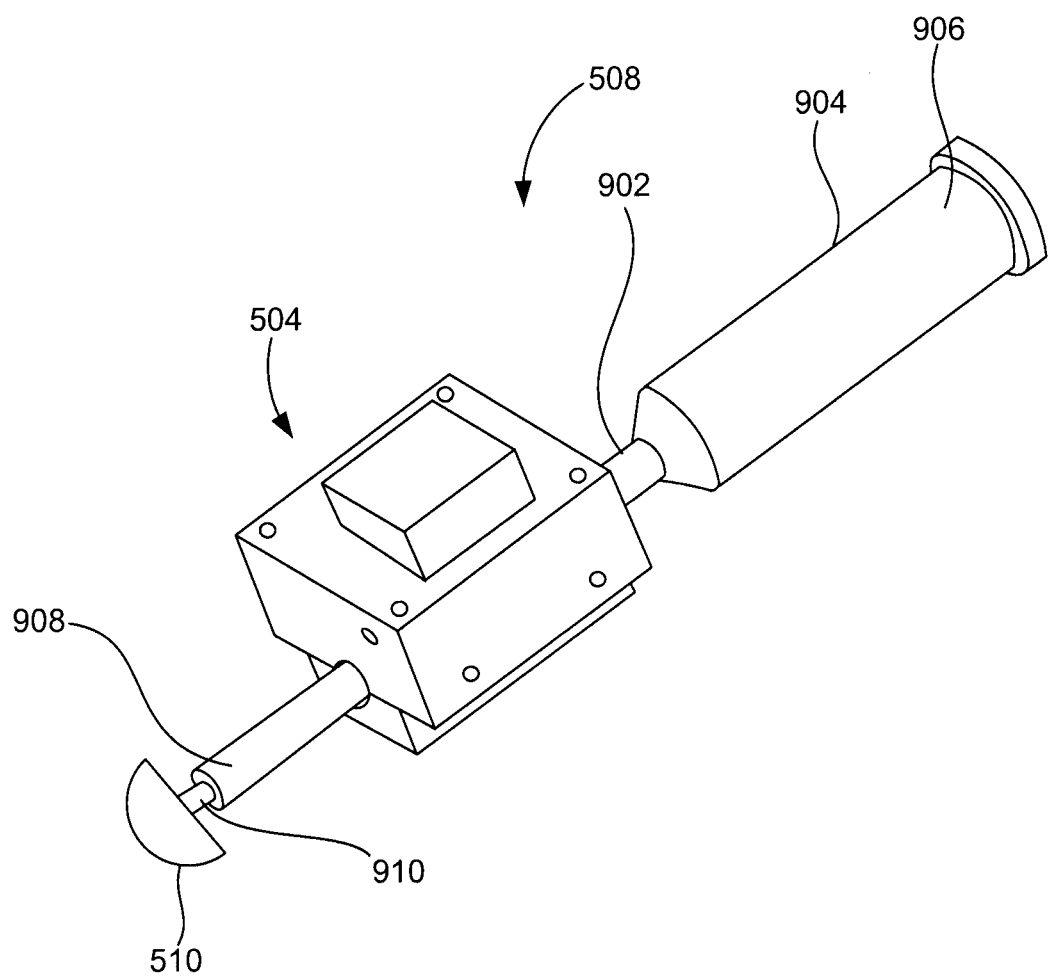
FIG. 9 is an isometric view of a surgical tool in accordance with at least one embodiment.

Reference is now made to FIG. 9, which illustrates a surgical tool 508 in accordance with an embodiment. As described above, the surgical tool 508 is used to insert the acetabular component or insert 510 into the patient's acetabulum. The surgical tool 508 may be any standard surgical tool used to perform this function. The surgical tool 508 typically includes a main shaft 902 and a handle 904 at the proximal end 906 of the main shaft 902. The acetabular component or implant 510 is attached to the distal end 908 of the shaft using any suitable means. For example, in some embodiments, the distal end 908 of the shaft 902 may include a spring-loaded interface 910 to which the acetabular component or implant 510 is attached.

The second active sensor 504 is attached to the surgical tool 508 in such a manner that it has a predetermined position and orientation with respect to the surgical tool 508 (and thus the acetabular component or insert 510). In one embodiment, the second active sensor 504 is attached to the shaft 902. However, it will be evident to a person of skill in the art that the second active sensor 504 may be attached to the surgical tool 508 at other locations and by other means.

Once the surgeon has placed the acetabular component or implant 510 at the desired orientation with respect to the pelvis using the surgical tool 508 (indicated by the display 514), the surgeon attaches the acetabular component or implant 510 to the pelvis. This may involve hammering the acetabular component or implant 510 into the acetabulum or using a biocompatible adhesive, such as a glue, to attach the acetabular component or implant 510 to the acetabulum, or both. In some embodiments, the surgical tool 508 may include a shock absorbing system to protect the second active sensor 504 from damage when the acetabular component or implant 510 is attached to the patient's pelvis.

Once the acetabular component or implant 510 is attached to the pelvis, the surgical tool 508 is detached from the acetabular component or implant 510 and removed from the patient's body. In one embodiment, the surgical tool 508 is unscrewed from the actetabular component or implant 510.

Figure 10:
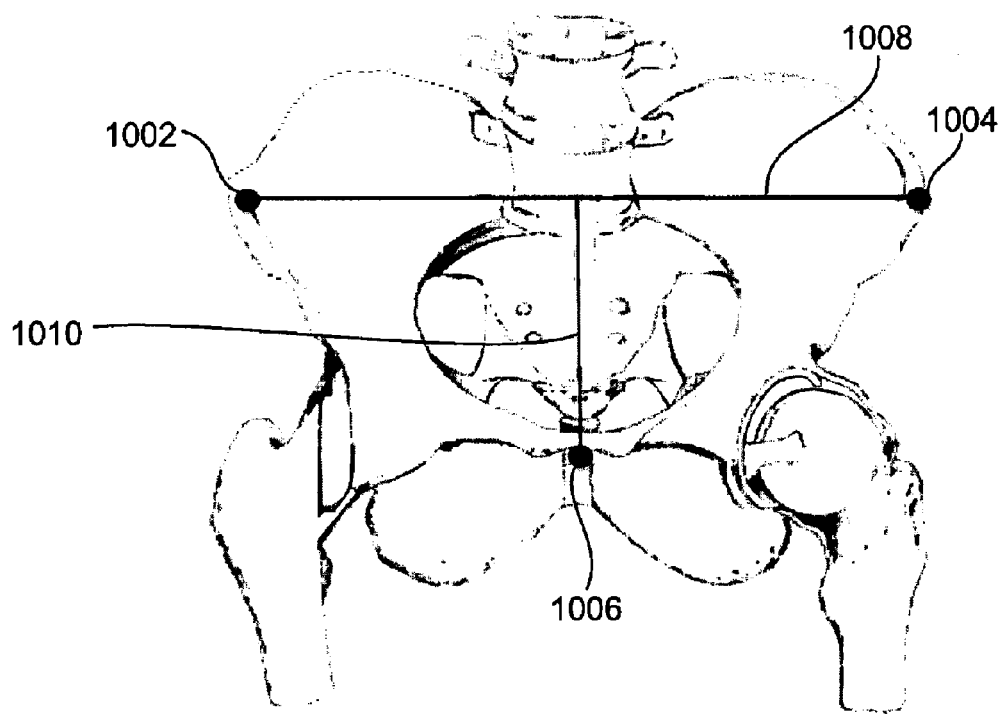
FIG. 10 is a front view of a pelvic bone illustrating a method for defining the pelvic reference plane in accordance with at least one embodiment.
Figure 11:
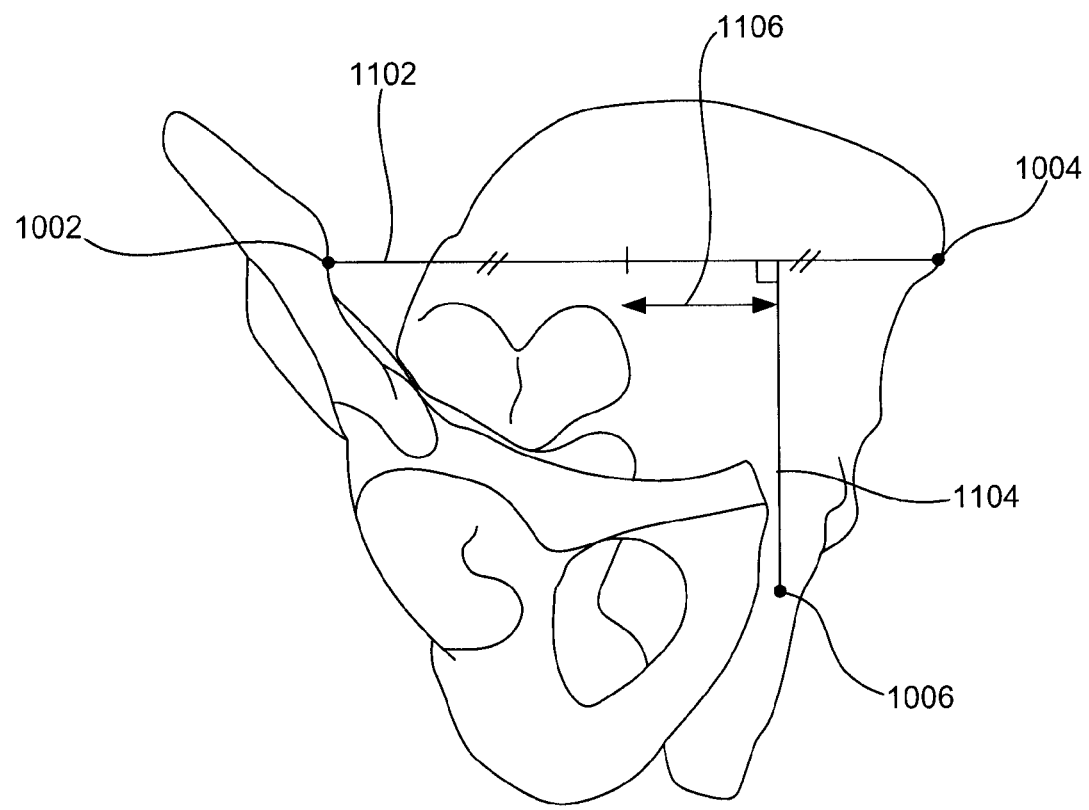
FIG. 11 is a semi-lateral view of a pelvic bone illustrating a method for defining the pelvic reference plane in accordance with at least one embodiment.

Reference is now made to FIGS. 10 and 11, which illustrate a front view and a semi-lateral view of a pelvis. These figures will be used to illustrate an exemplary method that may be implemented by the processor 512 to define the pelvic reference plane using three pelvic reference locations 1002, 1004 and 1006. In this exemplary method, the three pelvic reference locations are the right and left anterior superior iliac spines (ASISs) 1002 and 1004, and a position near the pubic region 1006.

As described above, the processor 512 uses distances between the pelvic reference locations to define the pelvic reference plane. In some embodiments, the distances between the pelvic reference locations may be determined or measured from one or more pre-operative scans (i.e. x-rays). In some embodiments, to more easily identify the pelvic reference locations on the pre-operative scans (i.e. x-rays) one or more of the pelvic reference locations may be marked with a physical marker prior to the conducting the scan (i.e. x-ray). For example, since the pubic region reference location 1006 is more difficult to identify on an x-ray than the ASISs 1002 and 1004, it may be beneficial to pre-mark the pubic region reference location 1006 by attaching a physical marker to the pubic region reference location 1006 prior to conducting the scan (i.e. x-ray). The physical marker may be attached to the pubic region reference location in any suitable fashion.

In this exemplary method, the measurements are taken from two pre-operative scans (i.e. x-rays). In one embodiment, one of the pre-operative scans (i.e. x-rays) is a frontal scan, and the second pre-operative scan (i.e. x-ray) is a diagonal scan. However, it will be evident to a person of skill in the art that other numbers and types of per-operative scans may be used. FIG. 10 represents a frontal x-ray of a pelvis, and FIG. 11 represents a diagonal x-ray of the same pelvis.

In this exemplary method, the exemplary distances that are used to define the pelvic reference plane are the inter-ASIS distance (the distance between the two ASIS pelvic reference locations 1002 and 1004) and the perpendicular distance between the pubic reference location 1006 and the ASISs 1002 and 1004. Both of these distances are measured on both pre-operative scans (i.e. x-rays). The inter-ASIS distance is identified with reference numeral 1008 in FIG. 10 and reference numeral 1102 in FIG. 11. Note that the inter-ASIS distance 1102 in FIG. 11 is taken at an angle so it will typically be shorter than the inter-ASIS distance 1008 of FIG. 10. The perpendicular distance is identified with reference numeral 1010 in FIG. 10 and reference numeral 1104 in FIG. 11. In addition, the distance between the intersection of 1102 and 1104 and the midpoint of 1102 is measured on the second pre-operative scan (i.e. x-ray). This distance is identified with reference numeral 1106.

These five distances (1008, 1010, 1102, 1104 and 1106) provide enough information to mathematically determine the pelvic reference plane on the patient's pelvis. As described above, the sensor positioning device 506 mechanically establishes this plane to position the first active sensor 502 in a predetermined position and orientation with respect to the pelvic reference plane.

Figure 12:
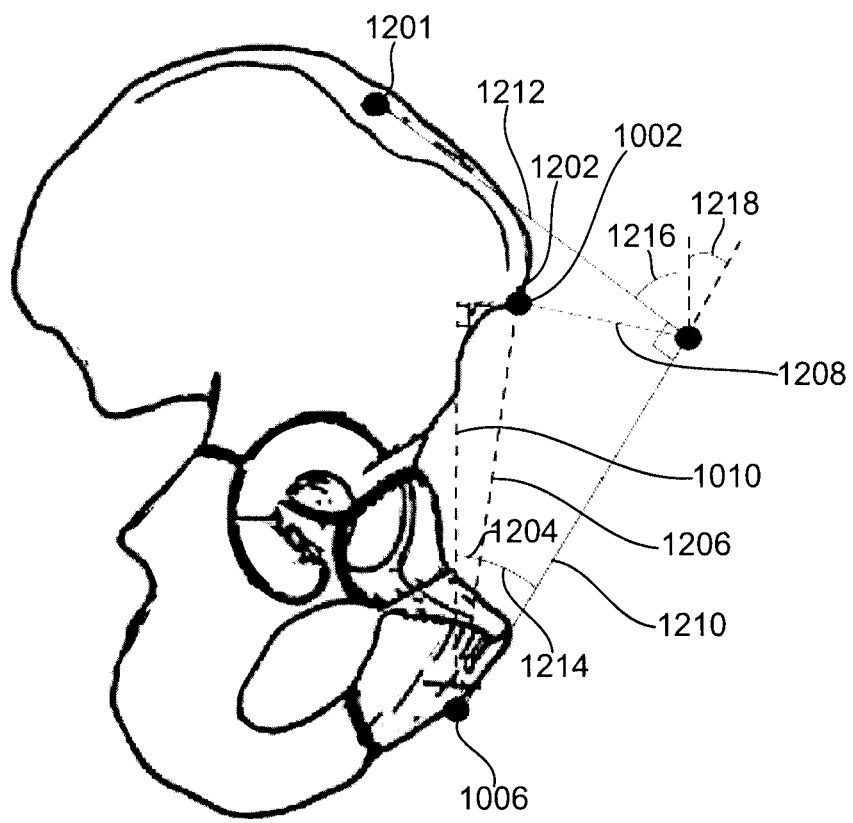
FIG. 12 is a side view of a pelvic bone used to illustrate a method of relating the first active sensor position to the pelvic reference plane in accordance with at least one embodiment.

Reference is now made to FIG. 12, which illustrates a lateral view of a pelvis. This figure will be used to illustrate an exemplary method used by the processor 512 to relate the first active sensor 502 position to the pelvic reference plane defined by the method described in relation to FIGS. 10 and 11. The position of the first active sensor 502 is identified with reference numeral 1201. As described above in reference to FIGS. 10 and 11, there are three reference points—the right and left ASIS 1002 and 1004 (not shown) and a pubic reference location 1006—that define the pelvic reference plane. As in FIG. 10, reference numeral 1010 represents the perpendicular distance between the pubic reference location 1006 and the right and left ASIS 1002 and 1004.

The distance 1202, also referred to as $D_{act}$ is calculated from equation (1) where A is the inter-ASIS distance 1008 of FIG. 10, C is the inter-ASIS distance 1102 of FIG. 11, and D is the intersection distance 1106 of FIG. 11:

$$D_{act} = \frac{D}{\cos\left[90° - \cos^{-1}\left(\frac{C}{A}\right)\right]} \tag{1}$$

The angle 1204, also referred to as β, is calculated from equation (2) where B is the perpendicular distance 1010 of FIG. 10:

$$\beta = \tan^{-1}\left(\frac{D_{act}}{B}\right) \tag{2}$$

The distance 1206, also referred to as l, is calculated from equation (3):

$$l = \sqrt{B^2 + D_{act}^2} \tag{3}$$

The distances 1208, 1210 and 1212, referred to as x, y and z respectively, correspond to the physical fixed lengths of components of the sensor positioning device 600. Specifically, distance 1208 corresponds to the length of the link members 614 and 616, distance 1210 corresponds to the length of the contact portion 618 of the arm 608, and distance 1212 corresponds to the length of the sensor portion 622 of the arm 608.

Angle 1214, also referred to as α, is calculated from equation (4):

$$\alpha = \cos^{-1}\left(\frac{l^2 + y^2 - x^2}{2ly}\right) \tag{4}$$

Angle 1216, also referred to as θ, is calculated from equation (5) which can be re-written as equation (6):

$$\theta = 90° - (\alpha + \beta) \tag{5}$$

Angle 1218, is the sum of angles 1204 (β) and 1214 (α).

It will be evident to a person of skill in the art that this information can be used to relate the first active sensor 502 orientation to the orientation of the pelvic reference plane.

Figure 13:
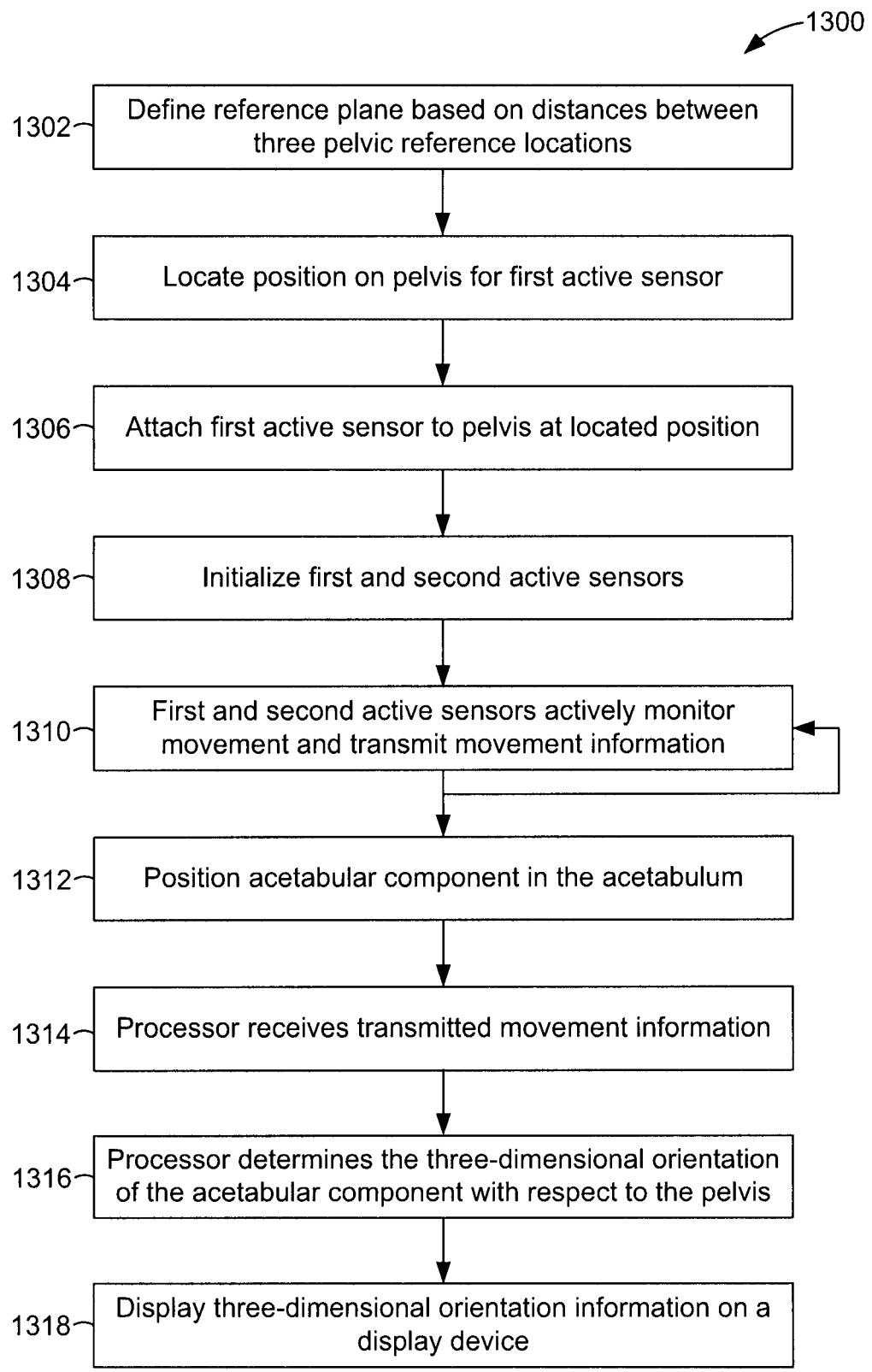
FIG. 13 is a flow chart of a method for aligning an acetabular implant during total hip arthroplasty using the system of FIG. 1 in accordance with at least one embodiment.

Reference is now made to FIG. 13, which illustrates a method 1300 for aligning an acetabular implant during total hip arthroplasty using the system of FIG. 5 in accordance with at least one embodiment. At step 1302, a pelvic reference plane is defined based on distances between three or more pelvic reference locations. The pelvic reference plane is preferably defined by a processor, such as processor 512, by inputting the distances into the processor.

As described above, the pelvic reference locations are anatomical landmarks on the pelvis and may include bony palpable landmarks, such as the right and left anterior superior iliac spine (ASIS) points, or non-palpable locations, such as the two pubic tubercles or the mid-point between the two pubic tubercles, or both. In one embodiment, the pelvic reference locations include both ASIS and a non-palpable point in the pubic area. In another embodiment, the pelvic reference locations include both ASIS and a palpable point on the iliac crest. It will be evident, however, to a person of skill in the art that other suitable anatomical landmarks may also be used as pelvic reference locations.

In some embodiments, the distances are manually measured from one or more pre-operative scans (i.e. x-rays) and then input into the processor. However, it will be evident to those of skill in the art that the distances may be determined using other suitable means. For example, the distances may alternatively be measured on the patient using a measuring device such as a tape measure. The distances are typically measured and input into the processor prior to surgery. Once the pelvic reference plane has been defined, the method 1300 proceeds to step 1304.

At step 1304, a position on the pelvis for the first active sensor is located using a sensor positioning device, such as sensor positioning device 600 or sensor positioning device 700. The sensor position is selected to have a predetermined relationship with the pelvic reference plane. By placing the first active sensor on the pelvis in a predetermined position and orientation with respect to the pelvic reference plane, changes in orientation to the pelvic reference plane can be tracked by changes in orientation of the first active sensor.

As described above, the sensor positioning device mechanically establishes the pelvic reference plane by lining up the contact members of the sensor positioning device with the pelvic reference locations. Once the sensor positioning device has been brought into contact with the three pelvic reference locations, the sensor positioning device identifies a position for the first active sensor that has a predetermined relationship to the pelvic reference plane. Once the position for the first active sensor has been located, the method 1300 proceeds to step 1306.

At step 1306, the first active sensor is attached to the pelvis at the located position using the sensor positioning device. Specifically, as described above, the sensor positioning device includes a guide, such as guide 612 or guide 712, to guide the first active sensor to the located position.

The specific configuration of the guide is dependent on the method used to attach the first active sensor to the pelvis. For example, where the first active sensor is attached to the pelvis using a bone screw, the guide 612 may be a hole or aperture that guides the bone screw to the predetermined position on the pelvis.

In addition to simply positioning the first active sensor on the pelvis, the first active sensor may also be oriented so that it has a predefined orientation with respect to the sensor positioning device. In some embodiments, the first active sensor has an orientation marker that can be manually aligned with an orientation marker on the guide to ensure that the first active sensor has a predefined orientation with respect to the sensor positioning device. In one embodiment, first active sensor may have an arrow or similar marker that is aligned with a similar arrow on the guide. In another embodiment, the guide may include a keyed slot which forces the bone screw to be inserted into the guide in a predetermined orientation.

At step 1308, the first active sensor (attached to the pelvis) and the second active sensor (attached to a surgical tool used to insert the acetabular component or insert), are initialized so that the first and second active sensors start the process with a predetermined orientation with respect to each other. In some embodiments, the initialization may involve starting the surgery with the second active sensor in a predetermined orientation. For example, the surgery may be started with the surgical tool in a horizontal position with the second active sensor pointing directly up. It should be noted that that the steps of the method 1300 do not necessarily need to be executed in the order specified. For example, the initialization may occur prior to attaching the first active sensor 502 to the pelvis. Typically, however, the initialization is performed before the processor starts receiving and processing movement information.

At step 1310, the first and second sensors actively monitor movement thereof and transmit the information to the processor. The movement information may be transmitted to the processor through a wired medium, such as an Ethernet, or wirelessly.

In one embodiment, the first and second active sensors are inertial sensors that use a combination of accelerometers and gyroscopes to detect the inertial movement of the sensor. In such an embodiment, the sensors typically sense and transmit information related to the angular acceleration and velocity of the sensor. In some embodiments, the sensors may also include a magnetometer for measuring the magnetic field surrounding the sensor. In still further embodiments, the sensors may also include an optical device, such as a camera, to monitor a physical marker remote to the sensor.

At step 1312, the acetabular insert or component is inserted into the acetabulum using the surgical tool. The method 1300 then proceeds to step 1314.

At step 1314, the processor (i.e. processor 512) receives the transmitted movement information from the first and second active sensors (i.e. first and second active sensors 502 and 504). As described above, the transmitted movement information may be transmitted from the first and second active sensors through a wired medium or wirelessly.

Upon receiving the movement information, the processor 512 typically performs pre-processing on the received information. Pre-processing may include performing filtering or conditioning or both. Typically the type of filtering performed by the processor is based on the type of active sensors employed. For example, gyroscopic sensors are subject to drift; therefore, where gyroscopic sensors are used, a high pass filter may be employed to compensate for the drift. The processor may also condition the received movement information for further processing. For example, the processor may adjust the received movement information to account for temperature etc. The pre-processing may be implemented by the processor in hardware (i.e. a field programmable gate array (FPGA)) or in software. In some embodiments, additional or alternate pre-processing may be performed by the active sensors prior to transmission. Once the signal has been received and the pre-processing is complete, the method 1300 proceeds to 1316.

At step 1316, the processor determines the three dimensional orientation of the acetabular implant with respect to the pelvis (and more specifically, determines angles of abduction and anteversion). Determining the three dimensional orientation of the acetabular implant with respect to the pelvis typically includes: (i) converting the received movement information into a format suitable for performing orientation calculations; and (ii) comparing the converted movement information from the first and second active sensors to determine the three dimensional orientation of the acetabular implant with respect to the pelvis (and more specifically determine angles of abduction and anteversion).

Converting the received movement information into a format suitable for performing orientation calculations typically includes converting the received movement information into rotational matrices, quaternions, or other suitable formats. The specific format is typically based on the type of active sensors used.

Once the received movement information has been converted into a suitable format, the processor determines the orientation of the two active sensors. The processor then uses the orientation of the first active sensor to determine the orientation of the pelvic reference plane and thus the pelvis. Specifically, since the first active sensor is in a predetermined position and orientation with respect to the pelvic reference plane, any changes in orientation to the first active sensor can be translated into changes in orientation to the pelvic reference plane, and thus the pelvis. A specific method for translating the orientation of the first active sensor to the orientation of the pelvic reference plane was described in reference to FIG. 12. The processor similarly uses the orientation of the second active sensor to determine the orientation of the surgical tool, and thus the acetabular component or implant. Specifically, since the second active sensor has a predetermined position and orientation with respect to the surgical tool, any changes in orientation to the second active sensor can be translated into changes in orientation to the surgical tool, and thus the acetabular component or insert.

Once the orientations of the pelvis and the acetabular component have been determined, the processor compares the orientations to determine the three dimensional orientation of the acetabular component or implant with respect to the pelvis. Specifically, since the first and second sensors begin the surgery with a predetermined orientation with respect to each other, any changes in orientation to either sensor can be used to determine changes in orientation of one sensor (and its corresponding device or body party) with respect to the other. In one embodiment, determining the three dimensional orientation of the acetabular component or implant with respect to the pelvis includes determining angles of abduction and anteversion. Once the orientation of the acetabular component or implant with respect to the pelvis has been determined, the method 1300 proceeds to step 1318.

At step 1318, the processor (i.e. processor 512) outputs the three dimensional orientation information to a display device, such as display device 514, to be displayed to the surgeon.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A device for positioning a sensor at a predetermined location and orientation on a bone of a patient, the device comprising:
   at least three contact members adapted for contacting anatomical landmarks providing reference locations for the bone; and
   a guide for positioning at least one sensor mount adapted for attaching the sensor on the bone at the predetermined location and orientation with respect to the at least three contact members, the sensor mount mateable with the sensor,
   wherein the guide is removable from the sensor mount when the sensor mount is attached to the bone, such that the device is removable from the patient.

2. The device of claim 1, wherein the guide comprises a first portion movably connected to a second portion, wherein the first portion is movable between an open position and a closed position, wherein in the closed position, the first portion is in engagement with the second portion to position the sensor mount in the predetermined position, wherein, in the open position, the first portion is disengaged from the second portion to permit removal of the device after the sensor mount is positioned at the predetermined location.

3. The device of claim 1, wherein the sensor mount is a bone screw.

4. The device of claim 1 further comprising a shaft between at least two of the at least three contact members.

5. The device of claim 4 further comprising an arm operatively connected to the shaft and wherein the guide is coupled to the arm and the arm is movable relative to the least two of the at least three contact members.

6. The device of claim 5, wherein the arm is rotatable about the shaft.

7. The device of claim 5, wherein the arm and shaft are fixedly attached and are rotatable with respect to the at least two of the at least three contact members.

8. The device of claim 5, wherein the arm is positioned at an end of the shaft.

9. The device of claim 4, wherein the arm is positioned between the at least two of the at least three contact members.

10. The device of claim 4, wherein the shaft is extendable.

11. The device of claim 10, wherein the shaft is a telescoping shaft.

12. The device of claim 1 wherein the guide slides off the sensor mount axially.

13. The device of claim 1 wherein the guide mechanically constrains the sensor mount to be inserted in a unique orientation.

14. The device of claim 1 wherein the guide includes an orientation marking for alignment of the sensor in the orientation.

15. The device of claim 1 wherein the bone is a pelvis.

16. The device of claim 1 wherein the sensor is attached to an iliac crest.

17. A method for attaching a sensor to a bone of a patient such that the sensor has a pre-determined position and orientation, comprising:
   contacting at least three contact members of the device of claim 1 with corresponding anatomical landmarks of the patient;
   while the device is contacted with the anatomical landmarks, attaching a sensor mount to the bone using the guide; and,
   in either order:
      attaching the sensor on the sensor mount; and
      removing the device from the sensor mount while leaving the sensor mount attached to the bone.

18. The method of claim 17 comprising using an orientation marker on the guide to match a with a corresponding marker for aligning the sensor mount in the pre-determined orientation.

19. The method of claim 17 wherein the pre-determined position and orientation is determined using pre-operative scans of the patient.

20. The method of claim 17 further comprising:
   pre-operatively configuring the device for the patient to align with the corresponding anatomical references determined using pre-operative scans of the patient.

21. The method of claim 20 wherein the device further comprises a shaft between at least two of the at least three contact members and an arm operatively connected to the shaft and wherein the guide is coupled to the arm and the arm is movable relative to the least two of the at least three contact members, wherein pre-operatively configuring the device comprises adjusting the position of at least one of the shaft, the arm, and the at least three contact members to account for patients of different sizes.

22. The method of claim 17 wherein the device further comprises a shaft between at least two of the at least three contact members and an arm operatively connected to the shaft and wherein the guide is coupled to the arm and the arm is movable relative to the least two of the at least three contact members, the step of contacting comprises contacting a first and second of the at least three contact members to corresponding anatomical references and moving the arm to bring a third of the at least three contact members into contact with a one of the anatomical references.

23. A device for positioning a sensor at a predetermined location and orientation on a bone of a patient, the device comprising:
   at least three contact members adapted for contacting anatomical landmarks providing reference locations for the bone; and
   a guide for positioning at least one sensor mount adapted for attaching the sensor on the bone at the predetermined location and orientation with respect to the at least three contact members, the sensor mount mateable with the sensor,
   wherein the guide comprises a first portion movably connected to a second portion,
   wherein the first portion is movable between an open position and a closed position,
   wherein in the closed position, the first portion is in engagement with the second portion to position the sensor mount in the predetermined position, and wherein, in the open position, the first portion is disengaged from the second portion to permit removal of the device after the sensor mount is positioned at the predetermined location.

* * * * *